(12) United States Patent
Boschi et al.

(10) Patent No.: US 12,162,877 B2
(45) Date of Patent: Dec. 10, 2024

(54) HUMAN DIHYDROOROTATE DEHYDROGENASE (HDHODH) INHIBITORS AND THEIR USE IN TARGETING ONCOLOGICAL DISEASES SENSITIVE TO PYRIMIDINE STARVATION

(71) Applicant: DRUG DISCOVERY AND CLINIC S.R.L., Turin (IT)

(72) Inventors: Donatella Boschi, Turin (IT); Marta Giorgis, Turin (IT); Marco Lucio Lolli, Turin (IT); Giovanni Martinelli, Mozzecane (IT); Giuseppe Saglio, Fubine (IT)

(73) Assignee: DRUG DISCOVERY AND CLINIC S.R.L. (IT)

( * ) Notice: Subject to any disclaimer, the term of this patent is extended or adjusted under 35 U.S.C. 154(b) by 850 days.

(21) Appl. No.: 16/972,456

(22) PCT Filed: Jun. 6, 2019

(86) PCT No.: PCT/EP2019/064861
§ 371 (c)(1),
(2) Date: Dec. 4, 2020

(87) PCT Pub. No.: WO2019/234186
PCT Pub. Date: Dec. 12, 2019

(65) Prior Publication Data
US 2021/0230156 A1 Jul. 29, 2021

(30) Foreign Application Priority Data
Jun. 6, 2018 (IT) .......................... 102018000006067

(51) Int. Cl.
*C07D 471/04* (2006.01)
*A61P 35/00* (2006.01)
(Continued)

(52) U.S. Cl.
CPC ............ *C07D 471/04* (2013.01); *A61P 35/00* (2018.01); *A61P 35/02* (2018.01); *C07D 487/04* (2013.01)

(58) Field of Classification Search
None
See application file for complete search history.

(56) References Cited

FOREIGN PATENT DOCUMENTS

WO    WO-2016073895 A1 *  5/2016  ........... A61K 31/519

OTHER PUBLICATIONS

U.S. Appl. No. 18/036,867 filed May 2023, Boschi, DOnatella.*
(Continued)

*Primary Examiner* — Eric Olson
(74) *Attorney, Agent, or Firm* — Procopio, Cory, Hargreaves & Savitch LLP; Brent A. Johnson; Erica A. Spence

(57) ABSTRACT

Compounds of formulae (I) and (II)

Formula (I)

(Continued)

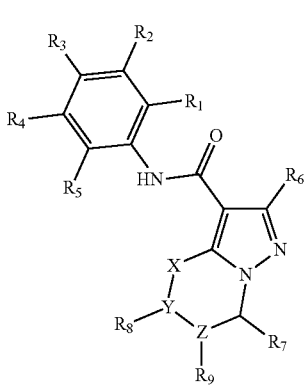

Formula (II)

which are novel inhibitors of human dihydroorotate dehydrogenase (hDHODH) and pharmaceutical compositions containing the compounds of formulae (I) and (II) are provided. A method for treating tumor diseases, including acute myelogenous leukemia (AML), triple-negative breast cancer, PTEN-mutant tumors, and KRAS-driven tumors by administering pharmaceutical compositions containing the compounds of formulae (I) and (II) is also provided.

26 Claims, 7 Drawing Sheets

(51) Int. Cl.
 *A61P 35/02* (2006.01)
 *C07D 487/04* (2006.01)

(56) References Cited

OTHER PUBLICATIONS

Lolli et al., "Use of human Dihydroorotate Dehydrogenase (hDHODH) Inhibitors in Autoimmune Diseases and New Perspectives in Cancer Therapy" Recent Patents on Anti-Cancer Drug Discovery vol. 13 pp. 86-105 (Year: 2018).*
Miyazaki et al., "Selective Cytotoxicity of Dihydroorotate Dehydrogenase Inhibitors to Human Cancer Cells Under Hypoxia and Nutrient-Deprived Conditions" Frontiers in PHarmacology vol. 9 pp. 1-13 doi: 10.3389/fphar.2018.00997 (Year: 2018).*
Godefridus J. Peters, "Re-evaluation of Brequinar sodium, a dihydroorotate dehydrogenase inhibitor" Nucleosides, Nucleotides and Nucleic Acids vol. 37 No. 12 pp. 666-678 https://doi.org/10.1080/15257770.2018.1508692 (Year: 2018).*
Lewis et al., "Development of ML390: A Human DHODH Inhibitor That Induces Differentiation in Acute Myeloid Leukemia" ACS Medicinal Chemistry Letters vol. 7 pp. 1112-1117 DOI: 10.1021/acsmedchemlett.6b00316 (Year: 2016).*
Sykes et al., "Inhibition of Dihydroorotate Dehydrogenase Overcomes Differentiation Blockade in Acute Myeloid Leukemia" Cell vol. 167 pp. 171-186 http://dx.doi.org/10.1016/j.cell.2016.08.057 (Year: 2016).*
International Search Report for International Patent Application No. PCT/EP2019/064861, mailed Jul. 19, 2019.
Vivek K. Vyas et al., Design, synthesis and pharmacological evaluation of novel substituted quinoline-2-carboxamide derivatives as human dihydroorotate dehydrogenase (hDHODH) inhibitors and anticancer agents, European Journal of Medicinal Chemistry, Jul. 23, 2014, pp. 385-393, vol. 82, Elsevier.
Stefano Sainas et al., Design, synthesis, biological evaluation and X-ray structural studies of potent human dihydroorotate dehydrogenase inhibitors based on hydroxylated azole scaffolds, European Journal of Medicinal Chemistry, Mar. 31, 2017, pp. 287-302, vol. 129, Elsevier.
Stefano Sainas et al., Targeting Myeloid Differentiation Using Potent 2-Hydroxypyrazolo[1,5-a]pyridine Scaffold-Based Human Dihydroorotate Dehydrogenase Inhibitors, Journal of Medicinal Chemistry, Jun. 25, 2018, pp. 6034-6055, vol. 61, No. 14, ACS Publications, USA.
Madak, J. T. et al., Revisiting the role of dihydroorotate dehydrogenase as a therapeutic target for cancer, Pharmacology & Therapeutics, Mar. 2019, pp. 111-131, vol. 195, Elsevier Inc.
Brown, K. K. et al., Adaptive Reprogramming of De Novo Pyrimidine Synthesis Is a Metabolic Vulnerability in Triple-Negative Breast Cancer, Cancer Discovery, Apr. 2017, pp. 391-399, vol. 7, Issue 4, American Association for Cancer Research, USA.
Mathur, D. et al., PTEN Regulates Glutamine Flux to Pyrimidine Synthesis and Sensitivity to Dihydroorotate Dehydrogenase Inhibition, Cancer Discovery, Apr. 2017, pp. 380-390, vol. 7, Issue 4, American Association for Cancer Research, USA.
Koundinya, M. et al., Dependence on the Pyrimidine Biosynthetic Enzyme DHODH Is a Synthetic Lethal Vulnerability in Mutant KRAS-Driven Cancers, Cell Chemical Biology, Jun. 21, 2018, pp. 705-717, vol. 25, Issue 6, Cell Press, Elsevier Ltd.
Leban J., Vitt D., Human dihydroorotate dehydrogenase inhibitors, a novel approach for the treatment of autoimmune and inflammatory diseases, Arzneimittelforschung, 2011, pp. 66-72, vol. 61, Issue 1, Thieme, DE.
Munier-Lehmann, H. et al., On Dihydroorotate Dehydrogenases and Their Inhibitors and Uses, Journal of Medicinal Chemistry, Mar. 1, 2013, pp. 3148-3167, vol. 56, Issue 8, ACS Publications, USA.
Herrmann, M. L. et al., Leflunomide: an Immunomodulatory Drug for the Treatment of Rheumatoid Arthritis and other Autoimmune Diseases, Immunopharmacology, May 2000, pp. 273-289, vol. 47, Issues 2-3, Elsevier Science BV.
Singh, A., Singh, P., Teriflunomide: a Novel Oral Disease-Modifying Agent under Investigation for the Treatment of Multiple Sclerosis, Journal of Drug Delivery & Therapeutics, 2016, pp. 97-102, vol. 6, No. 5, JDDT.
Peters, G. et al., Inhibition of Pyrimidine De Novo Synthesis by DUP-785 (NSC 368390), Investigational New Drugs, Sep. 1987, pp. 235-244, vol. 5, Issue 3, Martinus Nijhoff Publishers, Boston.
De Forni, M. et al., Phase I and Pharmacokinetic Study of Brequinar (DUP 785; NSC 368390) in Cancer Patients, European Journal of Cancer, 1993, pp. 983-988, vol. 29A, No. 7, Pergamon Press Ltd., Oxford, GB.
Joshi, A. S. et al.; Phase I Safety and Pharmacokinetic Studies of Brequinar Sodium after Single Ascending Oral Doses in Stable Renal, Hepatic, and Cardiac Allograft Recipients, The Journal of Clinical Pharmacology, Dec. 1997, pp. 1121-1128 vol. 37. Issue 12, ACCP, USA.
Schwartsmann, G. et al., Phase I Study of Brequinar Sodium (NSC 368390) in Patients with solid malignancies, Cancer Chemotherapy and Pharmacology, Sep. 1990, pp. 345-351, vol. 25, Issue 5, Springer Verlag.
Sykes, D. B. et al., Inhibition of Dihydroorotate Dehydrogenase Overcomes Differentiation Blockade in Acute Myeloid Leukemia, Cell, Sep. 22, 2016, pp. 171-186, vol. 167, Issue 1, Elsevier Inc.
Lewis, T. A. et al., Development of ML390: A Human DHODH Inhibitor That Induces Differentiation in Acute Myeloid Leukemia, ACS Medicinal Chemistry Letters, Sep. 28, 2016, pp. 1112-1117, vol. 7, Issue 12, ACS Publications, USA.
Tzelepis, K. et al., A Crispr Dropout Screen Identifies Genetic Vulnerabilities and Therapeutic Targets in Acute Myeloid Leukemia, Cell Reports, Oct. 18, 2016, pp. 1193-1205, vol. 17, Issue 4, Cell Press, USA.
Li, S. et al., Rational Design of Benzylidenehydrazinyl-Substituted Thiazole Derivatives as Potent Inhibitors of Human Dihydroorotate Dehydrogenase with in Vivo Anti-arthritic Activity, Scientific Reports, Oct. 7, 2015, pp. 14836-48555, vol. 5, Nature Research.
Munier-Lehmann, H. et al., Original 2-(3-Alkoxy-1H-pyrazol-1-yl)pyrimidine Derivatives as Inhibitors of Human Dihydroorotate Dehydrogenase (DHODH), Journal of Medicinal Chemistry, Jan. 6, 2015, pp. 860-877, vol. 58, Issue 2, ACS Publications, USA.

(56) References Cited

OTHER PUBLICATIONS

Zhu, J. et al., Design, Synthesis, X-Ray Crystallographic Analysis, and Biological Evaluation of Thiazole Derivatives as Potent and Selective Inhibitors of Human Dihydroorotate Dehydrogenase, Journal of Medicinal Chemistry, Jan. 12, 2015, pp. 1123-1139, vol. 58, Issue 3, ACS Publications, USA.

Pippione, A. C. et al., Substituted 4-Hydroxy-1,2,3-triazoles: synthesis, characterization and first drug design applications through bioisosteric modulation and scaffold hopping approaches, MedChemComm, 2015, 6, pp. 1285-1292, vol. 7, The Royal Society of Chemistry, London, GB.

Lucas-Hourani M. et al., Original 2-(3-Alkoxy-1H-pyrazol-1-yl)azines Inhibitors of Human Dihydroorotate Dehydrogenase (DHODH), Journal of Medicinal Chemistry, Jun. 6, 2015, pp. 5579-5598, vol. 58, Issue 14, ACS Publications, USA (Uploaded in Three Parts, pp. 1-20, pp. 21-50, 51-130).

Lolli, M. L. et al., New inhibitors of dihydroorotate dehydrogenase (DHODH) based on the 4-hydroxy-1,2,5-oxadiazol-3-yl (hydroxyfurazanyl) scaffold, European Journal of Medicinal Chemistry, Mar. 2012, pp. 102-109, vol. 49, Elsevier Masson SAS.

Baumgartner, R. et al., Dual Binding Mode of a Novel Series of DHODH Inhibitors, Journal of Medicinal Chemistry, Jan. 26, 2006, pp. 1239-1247 vol. 49, Issue 4, ACS Publications, USA.

Kakehi, A. et al., Synthesis Using Pyridinium N-Ylides. I. Synthesis and Some Reactions of Substituted 1-(Acetylimino)pyridinium Ylides, Bulletin of the Chemical Society of Japan, 1978, pp. 251-256, vol. 51, Issue 1, The Chemical Society of Japan, JP.

Ochi, H. et al., Studies of Heterocyclic Compounds. VIII. Synthesis and Tautomerism of 2-Hydroxypyrazolo[1,5-a]pyridine, Bulletin of the Chemical Society of Japan, 1976, pp. 1980-1984, vol. 49, Issue 7, The Chemical Society of Japan, JP.

Minkin, V. I. et al., The Tautomerism of Heterocycles: Five-membered Rings with Two or More Heteroatoms, Advances in Heterocyclic Chemistry, 2000, pp. 157-323, vol. 76, Alan R. Katritzky, Academic Press.

Pippione, A. C. et al., 4-Hydroxy-N-[3,5-bis(trifluoromethyl)phenyl]-1,2,5-thiadiazole-3-carboxamide: a novel inhibitor of the canonical NF-κB Cascade, MedChemComm, Sep. 1, 2017, pp. 1850-1855, vol. 8(9), The Royal Society of Chemistry, London, GB.

Williams-Noonan, B. J. et al., Free Energy Methods in Drug Design: Prospects of "Alchemical Perturbation" in Medicinal Chemistry, Journal of Medicinal Chemistry, Feb. 8, 2018, pp. 638-649, vol. 61, Issue 3, ACS Publications, USA.

Bonomo, S. et al., The role of fluorine in stabilizing the bioactive conformation of dihydroorotate dehydrogenase inhibitors, Journal of Molecular Modeling, Mar. 2013, pp. 1099-1107, vol. 19, Issue 3, Springer-Verlag, DE.

Cherwinski, H. M. et al., The Immunosuppressant Leflunomide Inhibits Lymphocyte Proliferation by Inhibiting Pyrimidine Biosynthesis, The Journal of Pharmacology and Experimental Therapeutics, Nov. 1, 1995, pp. 1043-1049, vol. 275, Issue 2, ASPET, USA.

\* cited by examiner

Leflunomide

Brequinar

1

2

3

HUMAN DIHYDROOROTATE DEHYDROGENASE (HDHODH) INHIBITORS AND THEIR USE IN TARGETING ONCOLOGICAL DISEASES SENSITIVE TO PYRIMIDINE STARVATION

CROSS-REFERENCE TO RELATED APPLICATIONS

This application is a National Stage Application of International Patent Application No. PCT/EP2019/064861, having an International Filing Date of Jun. 6, 2019, which claims the benefit of priority to Italian Patent Application No. 102018000006067, filed Jun. 6, 2018, the entire contents of which are hereby incorporated by reference herein.

FIELD OF THE INVENTION

The present invention relates to novel human dihydroorotate dehydrogenase (hDHODH) inhibitors and their use in the treatment of malignancies associated to certain tissue-types (e.g. acute myeloid leukemia (AML) and triple-negative breast cancer) or carrying certain mutational profiles (e.g. loss of PTEN or activated KRAS) that may be particularly sensitive to pyrimidine starvation due to inhibition of hDHODH.[1] In the case of acute myelogenous leukemia (AML), the mechanism associated to the efficacy of the use of hDHODH inhibitors is specifically related to the reactivation of the myeloid differentiation in AML cell lines, associated to an apoptotic mechanism.

Human dihydroorotate dehydrogenase (hDHODH) catalyzes the rate-limiting step in de novo pyrimidine biosynthesis, which converts dihydroorotate (DHO) to orotate (ORO). Having already been validated as a therapeutic target for the treatment of autoimmune diseases, such as rheumatoid arthritis and multiple sclerosis, hDHODH has also recently been identified as a relevant target in the treatment of triple-negative breast cancer,[2] PTEN-mutant tumors,[3] KRAS-driven tumors[4] and with acute myelogenous leukemia (AML); a disease for which the standard of intensive care has not changed over the last four decades. The connection with AML has paved the way for totally new perspectives in the treatment of the disease as well as in the hDHODH field. Presumably, all of these diverse malignancies converge on a similar pathway of metabolic reprogramming to drive their dependence on pyrimidine synthesis and sensitivity to DHODH-inhibition. The present invention relates to a novel class of inhibitors, based on an unusual carboxylic group bioisostere 2-hydroxypyrazolo[1,5-a]pyridine, that has been designed ideally starting from brequinar, one of the most potent known hDHODH inhibitors, using the innovative scaffold-hopping replacement technique. A combination of structure-based and ligand-based optimization strategies has led in particular to the production of compound 4, which shows brequinar-like hDHODH potency levels in vitro and is superior in terms of cytotoxicity and immunosuppression. Compound 4 also restores myeloid differentiation in leukemia cell lines at concentrations that are one log digit lower than those achieved in experiments with brequinar.

BACKGROUND OF THE INVENTION

Human dihydroorotate dehydrogenase (DHODH, EC 1.3.99.11) is a therapeutic target that has been validated for the treatment of autoimmune diseases and cancer.[5-6] hDHODH is located in the inner mitochondrial membrane and is a flavin-dependent enzyme involved in de novo pyrimidine biosynthesis. While a variety of hDHODH inhibitors have been synthesized over the years, the interesting activity of leflunomide and brequinar (FIG. 1), has led to them attracting a lot of attention.[7] Leflunomide and its metabolite teriflunomide, the only approved hDHODH-targeting drugs, have also been approved for the treatment of rheumatoid arthritis and other autoimmune diseases.[8-9] Brequinar, one of the most potent hDHODH inhibitors known to science, has been identified during a search for new potent hDHODH inhibitors that display clinical benefits similar to those of leflunomide, but without the associated side effects.[10] Unfortunately, brequinar was discarded as a therapeutic agent when submitted to clinical trials for cancer,[11] and the prevention of organ transplant rejection,[12] because of its side effects, a narrow therapeutic window and inconsistent pharmacokinetics.[6, 12-13] In the fall of 2016, two publications,[14-15] demonstrated the central role that hDHODH plays in acute myelogenous leukemia (AML), a disease for which standard intensive care has not changed over the last four decades.[16] AML, the most common acute leukemia in adults, is a cancer that affects the myeloid lineage of white blood cells. Leukemic cells lose their ability to differentiate into adult white blood cells meaning that immature cells, characterized by high proliferation potential, accumulate in the bone marrow and interfere with the production of normal blood cells. The disease progresses rapidly and is typically fatal within weeks or months if left untreated. The results of the above studies suggest that hDHODH plays a central role in the regulation of myeloid differentiation in both in vitro and in vivo models, and thus opens up totally new possibilities for AML treatment.

In a published study,[17] brequinar was used as an hDHODH inhibitor founding how it significantly induce myeloid differentiation, delay disease development and reduce the burden of leukemia-initiating cells in various AML mouse models, human cell line xenografts, patient-derived xenografts and syngeneic mouse models. The discovery of hDHODH's central role in AML immediately attracted the interest of pharmaceutical companies. Four hDHODH inhibitors are currently (May 2019) being investigated for the treatment of AML: brequinar itself, acquired by Clear Creek Bio from Bristol Myers Squibb in November 2017 and moved to Phase I clinical trial on October 2018; ASLAN 003, by ASLAN Pharmaceuticals, entered a Phase II clinical trial in November 2017; BAY2402234, by Bayer, entered Phase I preclinical trials in January 2018 (NCT03404726) and PTC299, that PTC Therapeutics moved to Phase Ib clinical trial in October 2018 to evaluate its safety, pharmacokinetics and preliminary evidence of antitumor activity in patients with relapsed/refractory acute myeloid leukemia (AML). The fact that a number of new hDHODH inhibitors have been reported in recent years,[5, 7, 18-22] and the increasing interest from industries both demonstrate that the need of developing new hDHODH inhibitors is an urgent issue.

The present inventors have recently introduced a new generation of hDHODH inhibitors that were designed via the scaffold-hopping replacement of brequinar's acidic moiety with a variety of acidic hydroxylated azoles.[17, 23] Three of these compounds (1-3), which are based on hydroxythiadiazole, hydroxytriazole and hydroxypyrazole respectively (FIG. 1), have shown high hDHODH inhibitory activity in vitro, with compound 1 being the best in the series with an $IC_{50}$ value of 16 nM. The X-ray crystallographic structures of 1-3 complexed with hDHODH have demonstrated how these acidic scaffolds, which show a variety of acidic properties,[21] play the role of brequinar's carboxylic group by interacting with Arg136 at hDHODH subsite 2.[24] Moreover, each system presented the possibility of establishing interactions with the small lipophilic pocket created by Val143 and Val134, known as subsite 4. When tested for antiproliferative activity, the compounds were found to be effective in the same concentration range as brequinar, while also presenting lower cellular cytotoxicity than the lead by only showing cytotoxic effects at 70-times the concentrations required to inhibit cell proliferation. The present invention represents the next step in the design process by describing a new series of potent hDHODH inhibitors that have been conceived using 2-hydroxypyrazolo[1,5-a]pyridine as the acidic scaffold.

SUMMARY OF THE INVENTION

2-Hydroxypyrazolo[1,5-a]pyridine is a system that is still relatively unexplored in literature. The present patent application reports its first scaffold-hopping use as a bioisostere of a carboxylic function. In the first series, besides investigating the moiety itself (compound 4-10, 18-22 FIG. 2), the inventors have also investigated the effect of introducing a methyl group into the pyridine ring in order to improve its lipophilic interaction with subsite 4 (compounds 5 and 6, FIG. 2) or replacing a pyiridine with a aliphatic pyperidine moiety as in compound 30. The second ring the biphenylic scaffold was also subject of investigation by inserting either polar (compound 31) or lipophilic (compounds 32 and 33) groups.

In the second series (compounds 8-10 and 29, FIG. 2), the inventors have replaced the biphenyl substituent with a more flexible diphenyl ether in order to improve its pharmacokinetic properties and provide more drug-like compounds. The theoretical design, synthesis, SAR, biological assays (cell viability, proliferation, cytotoxicity, immunosuppression and myeloid differentiation), physicochemical characterization and preliminary ADME profiles of the compounds are presented and discussed fully hereinafter.

Accordingly, a first aspect of the present invention is a 2-hydroxypyrazolo[1,5-a]pyridine scaffold-based hDHODH inhibitor of the general formula (I):

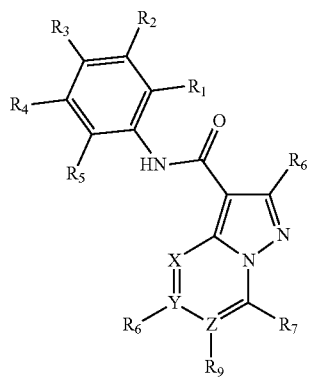

Formula (I)

wherein:
$R^1$, $R^2$, $R^4$ and $R^5$ are independently selected from the group consisting of a hydrogen atom, a halogen atom, a $C_1$-$C_4$ alkyl group, an alkyloxy group, an alkylthio group and a halo $C_1$-$C_4$ alkyl group;

$R^3$ is selected from the group consisting of phenyl, pyridil, pyridinil, phenoxy, pyridiloxy, pyridinoxy, thiophenoxy, thiophenyl, phenylthio, phenylcarboxamido, phenylaminocarbonyl group. If $R^3$ is an aromatic group, a substituent independently selected from halogen atom, alkyl, trifluoromethyl, trifluoromethoxy group can be present on the ring. If $R^3$ is an aliphatic group, a substituent independently selected from alkyl, trifluoromethyl, trifluoromethoxy group can be present on the ring;

$R^7$, $R^8$ and $R^9$ are independently selected from a hydrogen atom, a halo $C_1$-$C_4$ alkyl group, a thio $C_1$-$C_4$ alkyl group, an amino $C_1$-$C_4$ alkyl group, a $C_1$-$C_4$ alkyl group and a hydroxy $C_1$-$C_4$ alkyl group;

$R^6$ is selected from a $C_1$-$C_4$ alkyloxy group, an aciloxy group, a hydroxyl group, a thiol group or a salt thereof;

X, Y and Z are independently selected from a carbon atom or a nitrogen atom, wherein if X or Y or Z is nitrogen, the other two positions are carbon atoms.

According to a preferred embodiment, at least one of $R^1$, $R^2$, $R^4$ and $R^5$ is or contains a halogen atom. In the present description, a preferred halogen atom is a fluorine atom (F).

According to a particularly preferred embodiment of the invention, each of $R^1$, $R^2$, $R^4$ and $R^5$ is a fluorine atom and $R^3$ is phenyl.

In the definition of $R^6$, preferred salts are $Na^+$, $K^+$ or $Cs^{2+}$ salts.

In all of the aforementioned embodiments, a preferred $C_1$-$C_4$ alkyl group is a methyl group.

According to a particularly preferred embodiment of the invention, X, Y and Z are carbon (sp2) atoms.

Formula (Ia) illustrated herein below is a preferred embodiment of the invention wherein X=Y=Z in Formula (I) are carbon (sp²) atoms and $R_9$ is a proton:

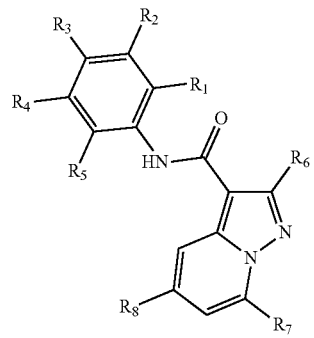

Formula (Ia)

Preferred compounds falling within the scope of formulae (I) and (Ia) are compounds 4-6, 8-10, 29 and 31-33 illustrated in FIG. 2.

Another aspect of the invention is a 2-hydroxypyrazolo [1,5-a]pyridine scaffold-based hDHODH inhibitor of the general formula (II):

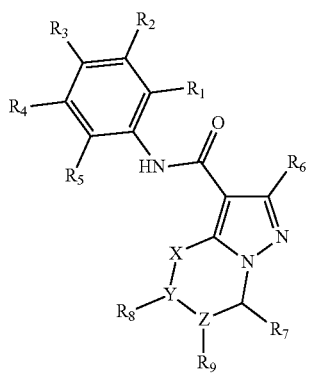

Formula (II)

wherein:

R$^1$, R$^2$, R$^4$ and R$^5$ are independently selected from the group consisting of a hydrogen atom, a halogen atom, a C$_1$-C$_4$ alkyl group, a alkyloxy group, a alkylthio group and a halo C$_1$-C$_4$ alkyl group;

R$^3$ is selected from the group consisting of phenyl, pyridil, pyridinil, phenoxy, pyridiloxy, pyridinoxy, thiophenoxy, thiophenyl, phenylthio, phenylcarboxamido, phenylaminocarbonyl group. If R$^3$ is an aromatic, a substituent independently selected from halogen atom, alkyl, a trifluoromethyl group, a trifluoromethoxy group can be present on the ring. If is R$^3$ an aliphatic group, a substituent independently selected from an alkyl group, a trifluoromethyl group, a trifluoromethoxy group can be present on the ring;

R$^7$, R$^8$ and R$^9$ are independently selected from a halo C$_1$-C$_4$ alkyl group, a thio C$_1$-C$_4$ alkyl group, an amino C$_1$-C$_4$ alkyl group, a C$_1$-C$_4$ alkyl group and a hydroxy C$_1$-C$_4$ alkyl group;

R$^6$ is selected from a C$_1$-C$_4$ alkyloxy group, an aciloxy group, a hydroxyl group, thiol group and a salt thereof;

X, Y and Z are independently selected from a carbon atom and a nitrogen atom; if X or Y or Z is nitrogen, the other two positions are carbon atoms.

According to a preferred embodiment of the invention, at least one of R$^1$, R$^2$, R$^4$ and R$^5$ is or contains a halogen atom. A preferred halogen atom is a fluorine atom (F).

According to a particularly preferred embodiment of the invention, each of R$^1$, R$^2$, R$^4$ and R$^5$ is a fluorine atom and R$^3$ is phenyl.

In the definition of R$^6$, preferred salts are Na$^+$, K$^+$ or Cs$^{2+}$ salts.

In all of the aforementioned embodiments of the invention, a preferred C$_1$-C$_4$ alkyl group is a methyl group.

According to a particularly preferred embodiment of the invention, both X, Y and Z are carbon sp$^3$ atoms.

Formula (IIa) illustrated herein below is a preferred embodiment of the invention wherein X=Y=Z are sp$^3$ C atoms and R$_9$ is a proton:

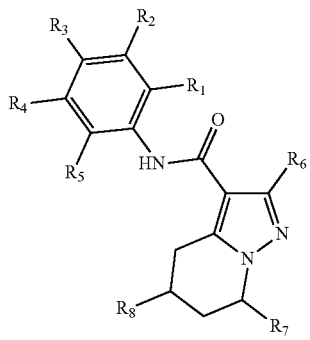

Formula (IIa)

Preferred compounds falling within the scope of formula (II) as well as formula (IIa) is compound 30 illustrated in FIG. 2.

Particularly preferred is compound 4, having the structural formula depicted herein below:

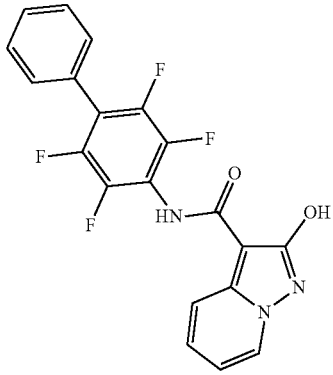

Compound 4

A third aspect of the present invention is a pharmaceutical composition comprising a 2-hydroxypyrazolo[1,5-a]pyridine scaffold-based hDHODH inhibitor of the general formula (I) as defined above and a pharmaceutically acceptable carrier, excipient or diluent.

A fourth aspect of the present invention is a 2-hydroxypyrazolo[1,5-a]pyridine scaffold-based hDHODH inhibitor as defined above in general formulae (I) and (II) and specific embodiments thereof, for use in a method of therapeutically treating a tumor disease, wherein the tumor disease is either a solid tumor or a leukemia; non-limiting examples of tumor teases that can be treated with the inhibitors of the invention are acute myelogenous leukemia (AML), triple-negative breast cancer, PTEN-mutant tumors, and KRAS-driven tumors.

The following experimental part is provided by way of illustration only and is not intended to limit the scope of the invention as defined by the appended claims.

BRIEF DESCRIPTION OF THE DRAWINGS

In the experimental part, reference is made to the following figures.

EXPERIMENTAL PART

Results and Discussion

Chemistry: Synthesis of Target Compounds 4-10

Figure 1:
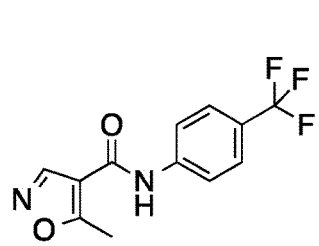
FIG. 1 shows the structures of prior art inhibitors leflunomide, brequinar and hydroxyazole analogues 1-3.
Figure 1:
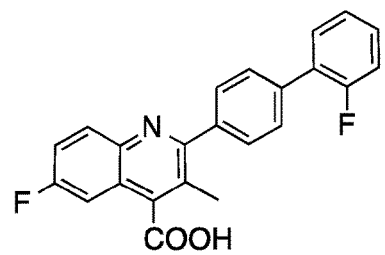
Figure 1:
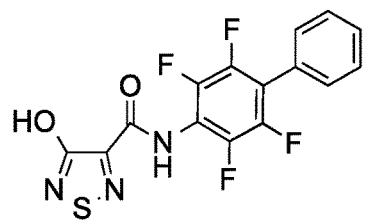
Figure 1:
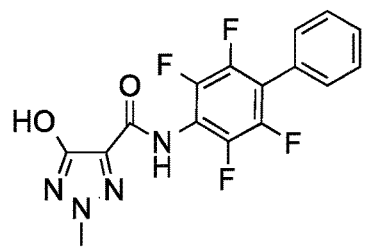
Figure 1:
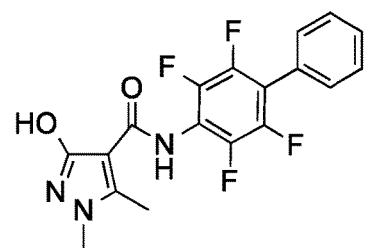
Figure 2:
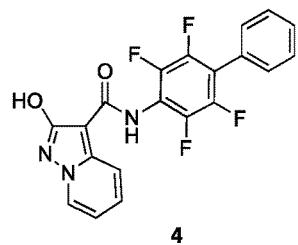
FIG. 2 shows the structures of compounds 4-10, 29-33 which are based on the 2-hydroxypyrazolo[1,5-a]pyridine scaffold (compound 7 does not fall within the scope of the invention).
Figure 2:
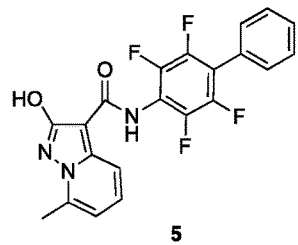
Figure 2:
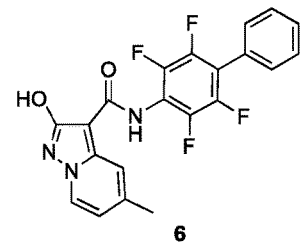
Figure 2:
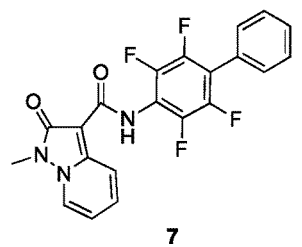
Figure 2:
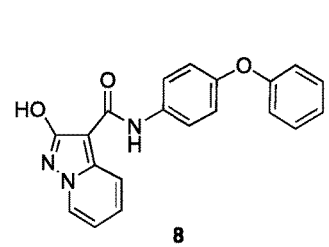
Figure 2:
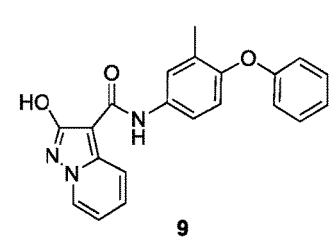
Figure 2:
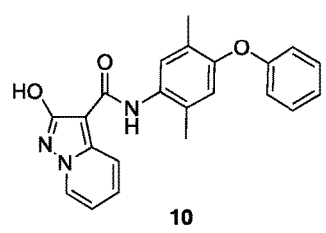
Figure 2:
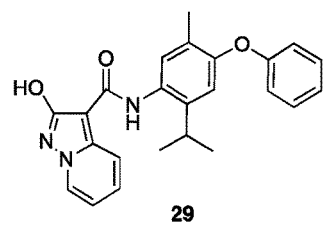
Figure 2:
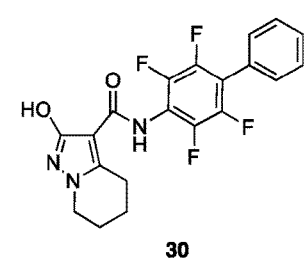
Figure 2:
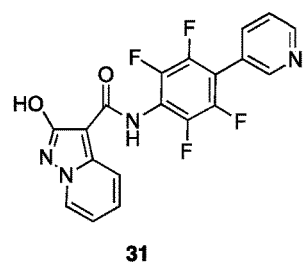
Figure 2:
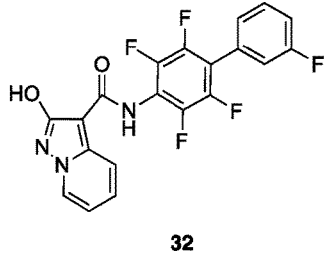
Figure 2:
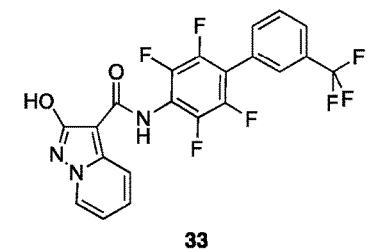
Figure 3:
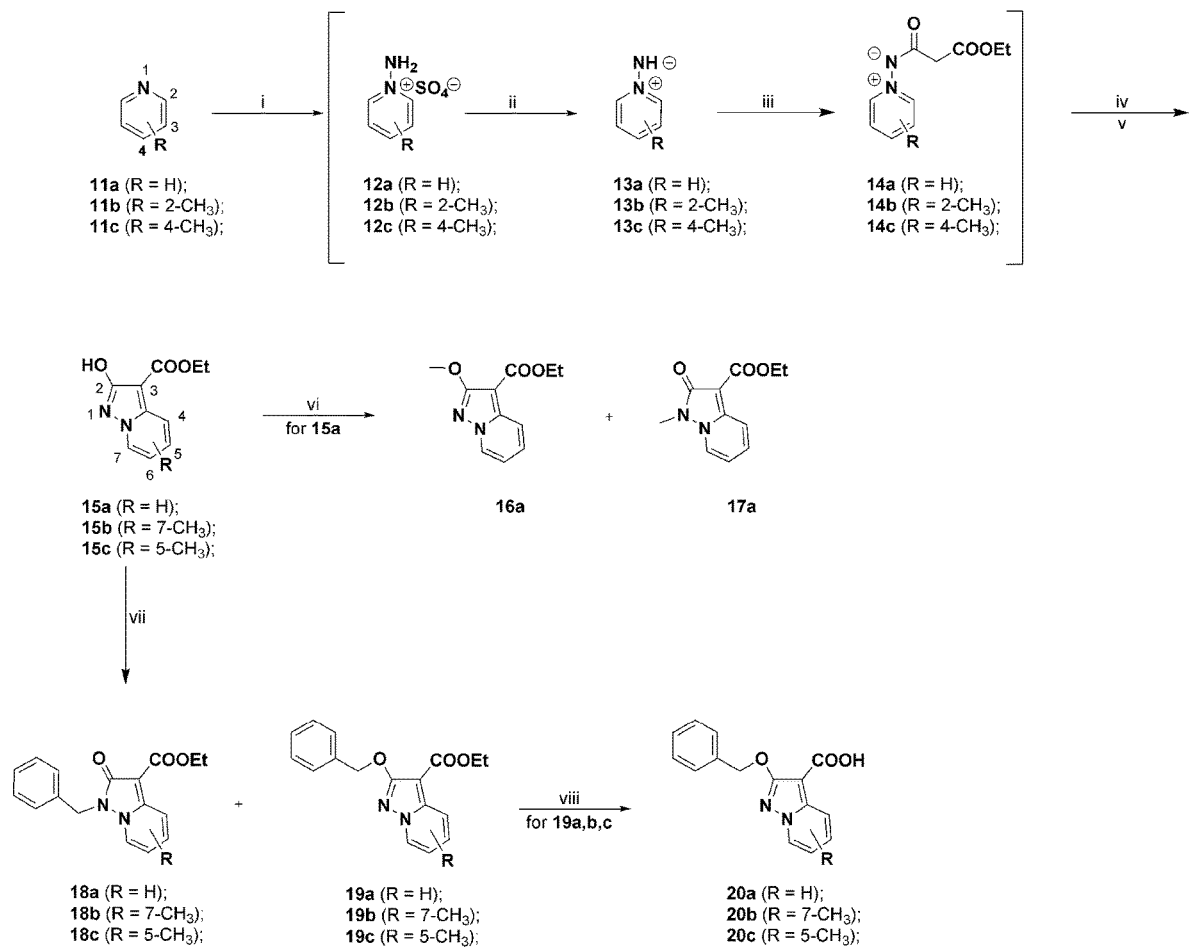
FIG. 3 shows the synthetic strategies for the preparation of substituted hydroxylated pyrazolo[1,5-a]pyridine intermediates. i) HOSA, H2O, 90° C.; ii) $K_2CO_3$, EtOH; iii) diethylmalonate, ethanol, 90° C.; iv) t-BuO-K+, dry THF v) 0.1N HCl; vi) $Cs_2CO_3$, MeI, dry THF, 40° C.; vii) Cs2CO3, BnBr, dry DMF, viii) 5M NaOH, ethanol, 70° C. (Scheme 1).

The chemical strategies used to produce the regiosubstituted, protected 2-hydroxypyrazolo[1,5-a]pyridine building blocks 20a-c, 17a, which are useful in the syntheses of compounds 4-10, are shown in Scheme 1 (FIG. 3). Compounds 15a,b,c were prepared, via a slight modification to a known procedure (Scheme 1),[25] starting from either pyridine or the corresponding substituted pyridines. Compounds 12a-c were obtained by aminating the corresponding substituted pyridines 11a-c, using hydroxylamine-O-sulfonic acid (HOSA) as the aminating reagent. The products were treated with $K_2CO_3$ to give the corresponding ylides 13 that were reacted with diethyl malonate in EtOH to give intermediate types 14, which were, in turn, converted into the desired compounds 15a-c, in the presence of a strong base (t-BuO⁻K⁺), in 18-21% overall yields.

Figure 4:
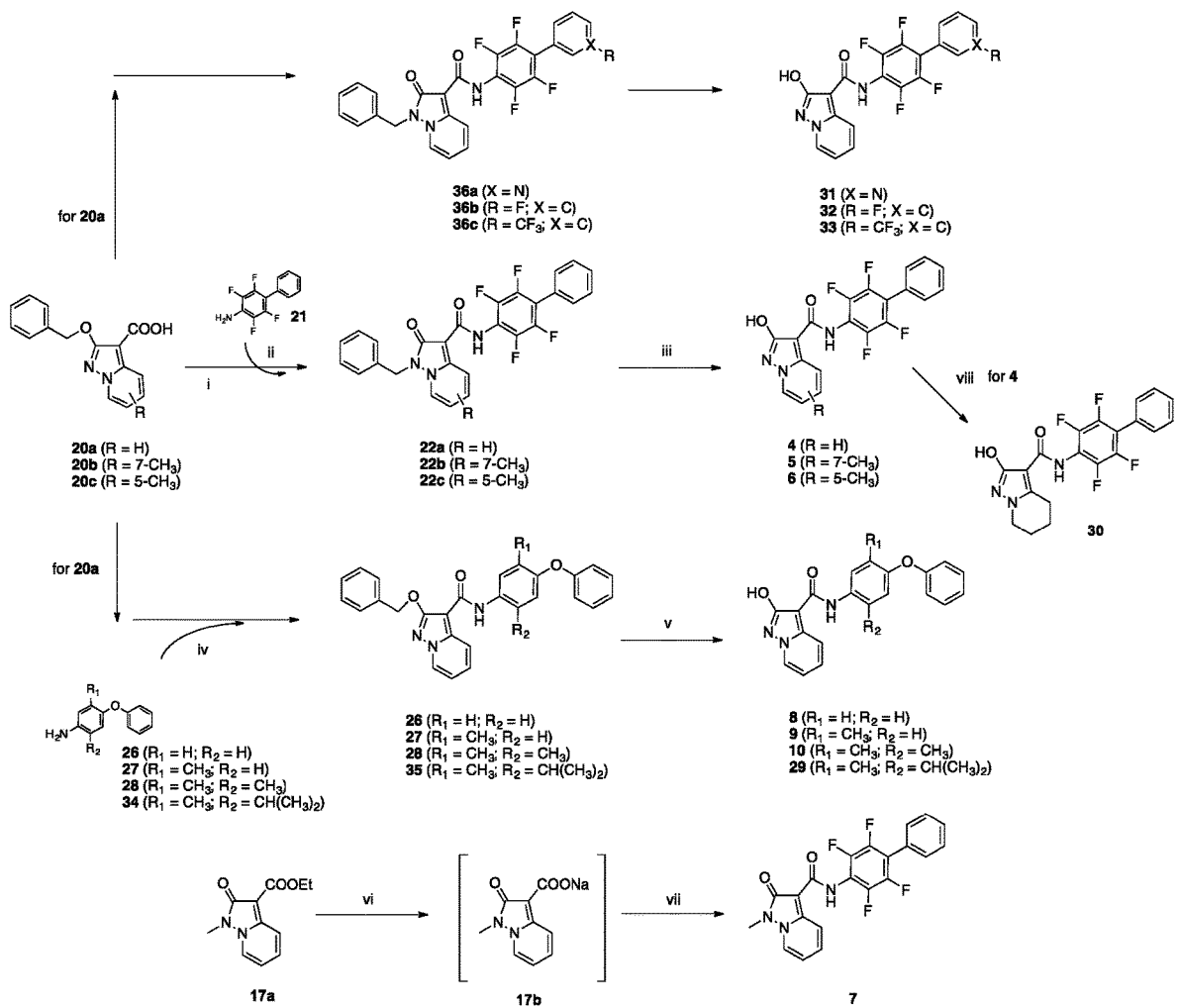
FIG. 4 shows the synthesis of targets 4-10, 29-33: i) oxalyl chloride, dry DMF, dry THF; ii) $AlMe_3$, dry toluene, reflux; iii) $H_2$, Pd/C, 37% HCl, ethanol; iv) dry toluene, reflux; v) $H_2$, Pd/C, dry THF, vi) 5M NaOH, ethanol, r.t. (Scheme 2).

Although some examples have been reported in the literature[26], the reactivity pattern that 2-hydroxypyrazolo[1,5-a]pyridines show towards alkylating agents has never been fully investigated. Both O- and N-alkylation patterns must always be considered,[17, 27] when considering the reactivity of substituted hydroxylated azoles. The type of heteroatom inside the heterocycle system and the choice of alkylating agent used usually govern the alkylation pattern.[17, 21, 28] Moving onwards in Scheme 1, the alkylation of 15a-c with benzyl bromide also gave the corresponding N-alkylated derivatives 18a-c (ratio 5-29%), besides desired O-alkylated compounds 19a-c, in each case. A similar result was obtained when methyl iodide was used as an alkylating agent on 15a, producing the methylated isomers 16a and 17a in 35% and 59% yields, respectively. 2D-NMR spectroscopy was used to univocally attribute the relative isomeric structures (see Supplementary material). Esters 19a-c were then hydrolyzed under basic conditions to afford the corresponding acids 20a-c in good yields, these were then used for the preparation of targets 4-6, 8-10, as described in Scheme 2 (FIG. 4). Starting from acids 20a-c (see Scheme 1 of FIG. 3), the corresponding acyl chlorides were obtained via treatment with oxalyl chloride in dichloromethane and used directly after drying without further purification. In order to improve their reactivity with acyl chlorides, 2,3,5,6-tetrafluoro-4-phenylaniline (21) or other biphenylanilines, was converted into its corresponding dimethylaluminum amide. The desired amides 22a-c or 36a-c were obtained in the 38-45% yield range. Interestingly, the benzylic protection transposed from the exocyclic oxygen to the endocyclic N1 nitrogen during coupling (see Supplementary for the characterization details). The $^{13}$C-NMR chemical shifts of the $CH_2$ benzylic nucleus were diagnostic for the structural attribution of N-benzyl or O-benzyl derivatives as for compounds 18a and 19a). On the other hand, the coupling of the acyl chloride, derived from 20a, with phenoxy anilines 23-25 afforded the expected O-benzyl-protected amides 26-28, as desired. This difference in reactivity led us to correlate the migration of the benzyl group with the presence of a Lewis acid in the reaction mixture. Compounds type 22a-c and 26-28 were then converted to desired target compounds 4-6, 8-10, 29-33 by applying room-pressure catalytic hydrogenation conditions. The same approach was applied to the preparation of 7. On this occasion, the acid obtained from the hydrolysis of 17b was quite an unstable compound, meaning that any isolation attempt resulted in its decarboxylation. The inventors avoided this decomposition by isolating the intermediate as a sodium salt and transforming it into the corresponding acyl chloride. The acyl chloride was stable enough to reach with the dimethylaluminum amide of 2,3,5,6-tetrafluoro-4-phenylaniline affording compound 7 in a 27% yield.

Inhibition of hDHODH and Structure-Activity Relationships (SAR)

First, the present inventors evaluated the recombinant hDHODH inhibition activity of compounds 4-10 and took teriflunomide, brequinar and the hydroxytriazole analogues 2,[17] as references (Table 1). Among the first-generation compounds 1-3, compound 2 showed the best balance between hDHODH potency and cell cytotoxicity and, for this reason, it was considered the most promising compound and included in this study.

TABLE 1

Biological effects of compounds 2, 4-10, brequinar and teriflunomide.

| Compound | hDHODH[a] IC$_{50}$ ± SE (μM) | Proliferation[b] IC$_{50}$ ± SE (μM) | Proliferation[b] IC$_{50}$ ± SE (μM) + Uridine | Cytotoxicity[c] (effect ≥30%) (μM) | Immuno-suppression[d] IC$_{50}$ ± SE (μM) | Immuno-suppression[d] IC$_{50}$ ± SE (μM) + Uridine |
|---|---|---|---|---|---|---|
| Brequinar | 0.0018 ± 0.0003 | 0.91 ± 0.07 | 94.17 ± 2.08 | 48.2 ± 0.8 | 3.74 ± 0.06 | 59.64 ± 2.18 |
| Teriflunomide | 0.388 ± 0.064 | 43.22 ± 1.24 | nd | 53 ± 3 | 54.3 ± 3.1[29] | nd |
| 2 | 0.045 ± 0.013 | 1.88 ± 0.06 | nd | >100 | 8.9 ± 0.7[29] | nd |
| 4 | 0.0012 ± 0.0002 | 0.75 ± 0.04 | 68.69 ± 2.35 | 60.4 ± 1.2 | 0.78 ± 0.06 | 57.15 ± 2.06 |
| 5 | 0.0043 ± 0.0005 | 0.82 ± 0.03 | 35.62 ± 0.98 | 41.3 ± 1.5 | 0.77 ± 0.08 | 46.84 ± 1.27 |
| 6 | 0.035 ± 0.003 | 1.56 ± 0.08 | 88.45 ± 1.48 | 48.6 ± 2.3 | 1.08 ± 0.10 | 52.39 ± 1.46 |
| 7 | >5 | nd | nd | nd | nd | nd |
| 8 | 0.760 ± 0.136 | 89.66 ± 1.64 | 95.63 ± 2.11 | >100 | 69.25 ± 2.47 | >100 |
| 9 | 0.480 ± 0.031 | 67.55 ± 1.21 | >100 | >100 | 35.26 ± 2.34 | >100 |
| 10 | 0.043 + 0.005 | 1.47 ± 0.06 | 55.13 ± 2.05 | >100 | 0.84 ± 0.16 | 74.69 ± 1.63 |

The effect of the compounds (expressed as IC$_{50}$ value, except for cytotoxicity), on
[a]hDHODH, in vitro assay;
[b]inhibition of cell proliferation (Jurkat T cells);
[c]cytotoxicity, concentration of compounds causing a significant (≥30%), cytotoxic effect (Jurkat T cells);
[d]inhibition of PHA-stimulated PBMC proliferation.
The "nd" notation indicates that the compound was not tested in that specific assay.

2-Hydroxypyrazolo[1,5-a]pyridine analogue 4 (IC$_{50}$=1.2 nM), was found to be the most potent compound in the series, as it was 320 times more potent than teriflunomide (IC$_{50}$=388 nM), and just comparable to brequinar (IC$_{50}$=1.8 nM) in the enzymatic assay, which proves the validity of this approach Further, the present inventors focused their attention on the possibility of decorating the "pyridine" part of the bioisosteric scaffold 4, to add an interaction with the small lipophilic pocket created by Val134 and Val143 (subsite 4). The study was based on a computational approach, led by the result of Molecular Dynamics (MD) free energy perturbation (FEP)[30] The four available positions of 4, indicated in Table 2, were explored using MD/FEP methyl and chlorine scans to identify the most promising sites for a beneficial hydrogen substitution.

TABLE 2

MD/FEP results of the change in calculated free energy of binding (in kcal/mol), and the computed uncertainty, for the introduction of chlorine and methyl substituents on the 2-hydroxypyrazolo[1,5-a]pyridine motif of compound 4.

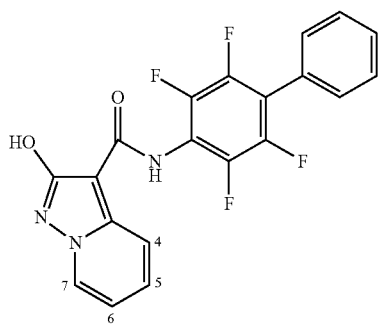

| | H to Cl ΔΔG (kcal/mol) | H to CH$_3$ ΔΔG (kcal/mol) |
|---|---|---|
| C4 | −0.35 ± 0.02 | 1.49 ± 0.07 |
| C5 | −0.48 ± 0.02 | 1.19 ± 0.07 |
| C6 | 0.87 ± 0.02 | 2.59 ± 0.07 |
| C7 | −1.43 ± 0.02 | 0.15 ± 0.09 |

The obtained ΔΔG values indicates that chlorine group is generally preferred over methyl in all the positions, since negative values represent an increasing in binding affinity. Among the four sites, position 7 is the most profitable for a substitution as presents the lower energy values, −1.43 for the chlorine and only a marginal effect on the energy for the methyl group (0.15). Replacement of hydrogen in position 6 is the less favorite accord to the higher positive energies values for chlorine (0.87) and methyl (2.59). Position 4 and 5 show comparable behavior, substitution in 5 is only slice well tolerated then in 4 for both groups.

Moving to experimental and taking in account MD/FEP results, the two most tolerated positions, 5 and 7, have been considered to be modulated. Since the discussed chlorine derivates of 4 are not yet synthetically accessible in this study, derivate with a methyl substituent in positions 7 and 5 were synthetized (Scheme 1), leading to compounds 5 and 6, respectively. Whereas the substitution of position 5 decreased the activity by 25 fold (6, IC$_{50}$=35 nM), as compared to 4, the substitution of position 7 provided a similar profile (5, IC$_{50}$=4.3 nM). With compound 30 (IC$_{50}$=5.9 nM) was validated the possibility to replace the pyrazole-pyridine with pyrazolepiperidine bioisosteric scaffold without loosing binding affinity. Three compounds (31-33) where dedicated to the decoration of the second ring the biphenyl scaffold; in particular the meta position, because not involved in any binding, was identified for the possible introduction of substituents able to improve the structure drug-like profile. In the pyridine analogue (compound 31), was investigated the possibility to increase the general structure solubility, a quite problematic weakness of compound 4. In compound 32 and 33, the presence of lipophilic moieties (F and CF$_3$) improved the general structure lipophilicity (Log D>3) without loosing affinities (IC$_{50}$=2.0 and 2.3 nM respectively). This is quite relevant because log Ds higher of 2.5 were correlated to a better permeation the structure toward the mitochondrial target site.

In the second series (compounds 8-10 and 29 Table 2), the replacement of the biphenylic substituent was investigated in an attempt to improve pharmacokinetic properties and obtain more drug-like compounds. In our studies,[17, 23] optimal interaction with lipophilic subsite 1 was only guaranteed with tetrafluoro substitution on the first ring. Conformational analyses,[31] underlined the role of incremental fluorine substitution on the first ring in stabilizing the brequinar-like binding mode, which has previously been found to be connected with higher inhibitory potency.[24] For example, the removal of two or three fluorine atoms from the biphenylic scaffold of triazole analogue 2 resulted in a dramatic drop in inhibitory activity.[17] However, the presence of the tetrafluorobiphenylic substituent is detrimental for the solubility of our derivatives. The inventors therefore decided to design analogues that lacked a biphenylic scaffold in order to investigate novel possibilities. Although a dramatic drop in activity was observed in moving from 4 ($IC_{50}$=1.2 nM), to 8 ($IC_{50}$=760 nM), the biphenylic replacement seems to be required for activity to occur. The addition of a methyl group to the position 3 of the first ring (compound 9), led to activity moving slightly towards the teriflunomide range ($IC_{50}$=480 nM), while adding a second methyl to the position 6 (compound 10), finally caused a nM range to be obtained ($IC_{50}$=43 nM). On the basis of these results, the inventors envisioned that the increased rigidity granted by the double methyl substitution and the increase in hydrophobicity might be crucial for activity. These results supported the design of compound 29 where the increased rigidity is granted by the double substitution on the first ring. In particular, an optimal affinity toward subsite 1 is granted by the presence in the first ring of an isopropyl moiety; compound 29 with $IC_{50}$=6.9 nM is the most potent compound the phenylphenoxy series.

Cell Based Assays
Proliferation, Cytotoxicity and Immunosuppression on Jurkat Cells After evaluating compounds 4-10 for their ability to inhibit recombinant hDHODH in vitro, active compounds 4-6 and 8-10 were tested for their effects on cell proliferation in Jurkat T cells (Table 1). The stability of compounds under the applied experimental conditions was also checked and they were all found to be stable. The potent hDHODH in vitro activity observed for compounds 4 and 5 was translated into a potent antiproliferative effect, which was slightly superior to that of brequinar itself in both cases. Compounds 6 and 8-10 displayed similar profiles although weaker hDHODH potency was reflected in weaker antiproliferative effects. Besides 4 and 5, 6 and 10 also outperformed teriflunomide, with both showing antiproliferative effects that were 30 times more potent. The DHODH-dependence of the antiproliferative effects of compounds 4-6 and 8-10 were tested by also assaying their activity in the presence of 100 µM uridine.[32] As shown in Table 1, the antiproliferative effects were reverted by the addition of exogenous uridine, which strongly indicates that the compounds act as pyrimidine biosynthesis inhibitors, and thus inhibit Jurkat cell proliferation via this mechanism. The exception to this is 8, which is probably too weak as hDHODH inhibitor to produce a reverse uridine-mediated effect. In order to evaluate whether the antiproliferative effects resulted from cell death, cytotoxicity was evaluated on Jurkat T cells using the CellTox green assay and the concentration of compounds that was able to cause 30% cell death were detected. Compound 4 had no negative effect on cell viability up to 60 µM, while 5 was found to be cytotoxic in a concentration similar to brequinar. Intriguingly, no negative effect on cell viability was observed in compounds 8-10, for which a diphenylether was used to introduce subsite 1 interactions, even when they were tested at a concentration of 100 µM. This result is quite interesting as it shows how promising drug-like profiles can be obtained using this moiety.

In order to investigate whether the immunosuppressive activity of compounds, their effect on the proliferation of phytohaemagglutinin (PHA)-activated peripheral blood mononuclear cells (PBMCs) was evaluated and compared with that of brequinar. As shown in Table 1, the antiproliferative effect of brequinar is 10 times greater than that of teriflunomide (3.74 and 54.3 µM, respectively), which confirms earlier research. It was observed that potent activity against hDHODH correlates with the potent inhibition of activated PBMC proliferation for all tested compounds. This inhibition, however, can be reversed by the addition of exogenous uridine, suggesting that the immunosuppressive activity of the compounds may be due to the inhibition of de novo pyrimidine nucleotide synthesis.

Proliferation, Cytotoxicity and Myeloid Differentiation in Leukemia Cells

Figure 5:
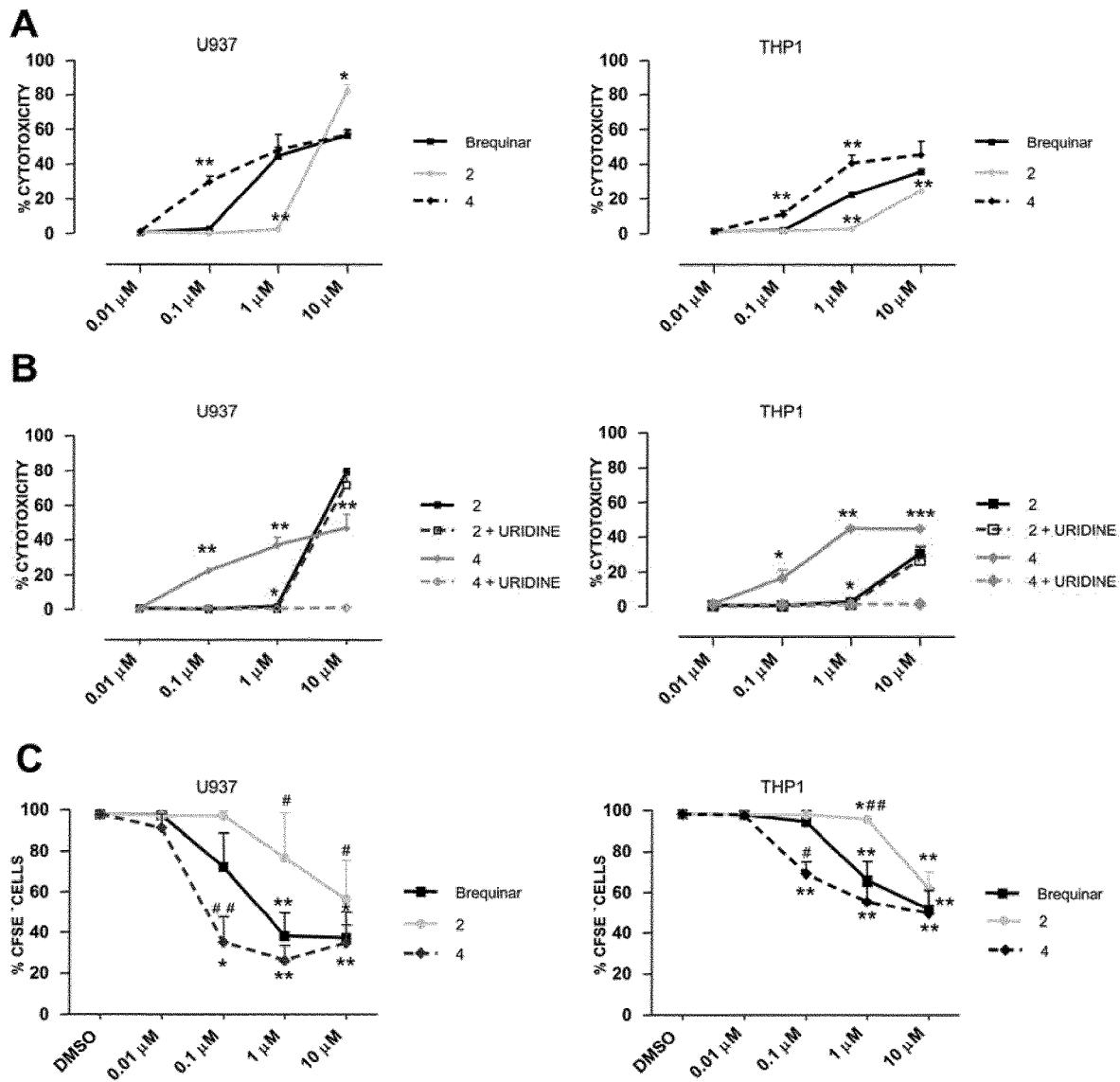
FIG. 5 shows the results of cytotoxicity assays. A) Cytotoxicity induced by different concentrations of brequinar, compound 2 and 4 on U937 and THP1. Statistical significance: *$p<0.05$; **$p<0.01$ between our compounds and brequinar. B) Cytotoxicity is totally reversed when uridine is added to compound 4, but not to compound 2, both in U937 and THP1. Statistical significance: *$p<0.05$; **$p<0.01$ between each compound±uridine. Uridine was added at 100 μM concentration. C) Proliferation inhibition exerted by different concentrations of brequinar, compound 2 and 4 on U937 and THP1. Statistical significance: *$p<0.05$; $p<0.01$; *$p<0.001$ between treated and untreated cells (DMSO only). #$p<0.05$ between our compounds and brequinar. DMSO=dimethyl sulfoxide, i.e., the solvent of all tested compounds.

Moving forward in their study, the present inventors evaluated the effects of our hDHODH inhibitors on two AML cell lines (U937 and THP1). The inventors decided to compare compound 4, judged as the best compromise between potency and cytotoxicity, triazole 2, the top compound from the first series which displays very low cytotoxicity, and brequinar, which was used as a positive control. In the first experiments, the inventors evaluated cell viability using CFSE-based experiments. As shown in FIG. 5A, both compound 4 and brequinar showed strong and concentration-dependent cytotoxicity, while compound 2 was only able to induce cell death at high doses.

Figure 6:
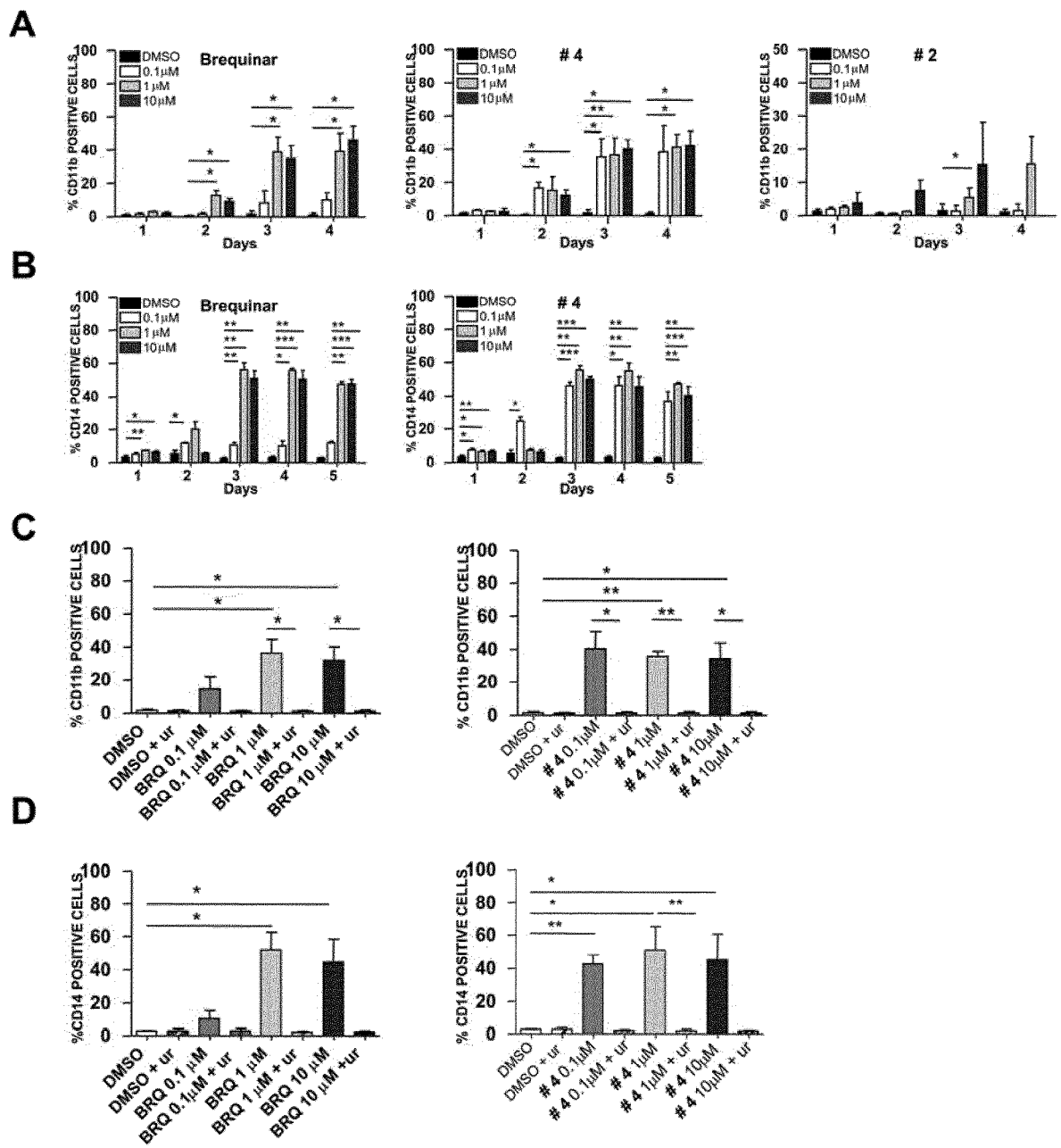
FIG. 6 shows the results of differentiation assays. A) Kinetic of differentiation induced by various concentrations of brequinar, compound 4 and 2, on U937, expressed as the proportion of CD11b positive cells. B) Kinetic of differentiation induced by various concentrations of brequinar and compound 4 on THP1, expressed as the proportion of CD14 positive cells. C) The differentiation induced on U937 by brequinar (left panel) and compound 4 (right panel) is reversed when uridine is added. The differentiation analysis is performed at day 3. D) The differentiation induced on THP1 by brequinar (left panel) and compound 4 (right panel) is reversed when uridine is added. The differentiation analysis is performed at day 3. DMSO indicates cells treated with dimethyl sulfoxide only. #4=compound 4; #2=compound 2; BRQ=brequinar; ur=uridine. Uridine was added at 100 μM concentration in all experiments. Statistical significance: *$p<0.05$; $p<0.01$; *$p<0.001$.

Compound 4 cytotoxicity was totally reversed when uridine was added, but this was not the case with compound 2 (FIG. 5B). This suggests that cytotoxicity may only be ascribed to hDHODH inhibition for compound 4, while 2 was associated with off-target toxicity at high doses. Moreover, cytotoxicity against U937 was slightly more evident than that against THP1, which probably reflects the heterogeneity of AML. CFSE-based proliferation assays were also performed and, as expected, compound 4, brequinar and, to a lesser extent, compound 2, all greatly reduced cell proliferation, as shown in FIG. 5C. Interestingly, compound 4 seemed to be more effective than brequinar at lower concentrations both in proliferation and cytotoxicity experiments. While results from the proliferation assays were expected, cytotoxicity data, at first sight, contradicted the Jurkat-T cell experiments, which had shown our compounds' very low toxicity. However, as mature cells have a much shorter half-life than immature ones, the inventors hypothesized that the considerable cytotoxicity observed in AML cell lines, but not in Jurkat-T cells, had to be ascribed to the differentiation induced in leukemic cells by hDHODH inhibitors. The inventors therefore investigated the differentiation effect induced by compounds 2, 4 and brequinar on our AML cell lines at several concentrations. The differentiation process was tracked by analyzing CD11b and CD14 expression, as these antigens are typically present in mature myeloid cells. In particular, cell differentiation could be best evaluated with CD11b on U937 and with CD14 on THP1; similar, but less prominent results were obtained with CD11b on THP1. Our experiments clearly demonstrated that both compound 4 and brequinar induced a strong differentiation in U937 and THP1 cells, as shown in FIG. 6A, 6B. After the treatment with these compounds, in fact, the expression of CD11b and CD14 increased significantly day by day, according to drug concentrations.

Notably, compound 4 induced a differentiation effect that was comparable to that of brequinar at a 1-log inferior concentration. Compound 2, on the other hand, only induced a mild CD11b increase in U937 cells that only occurred at high doses (10 µM), where it was associated with significant cell death. These data, together with the cytotoxicity results, indicated that compound 2 was not able to induce myeloid differentiation and caused off-target toxicity at high doses. For this reason, compound 2 was excluded from further experiments with THP1 and uridine.

Figure 7:
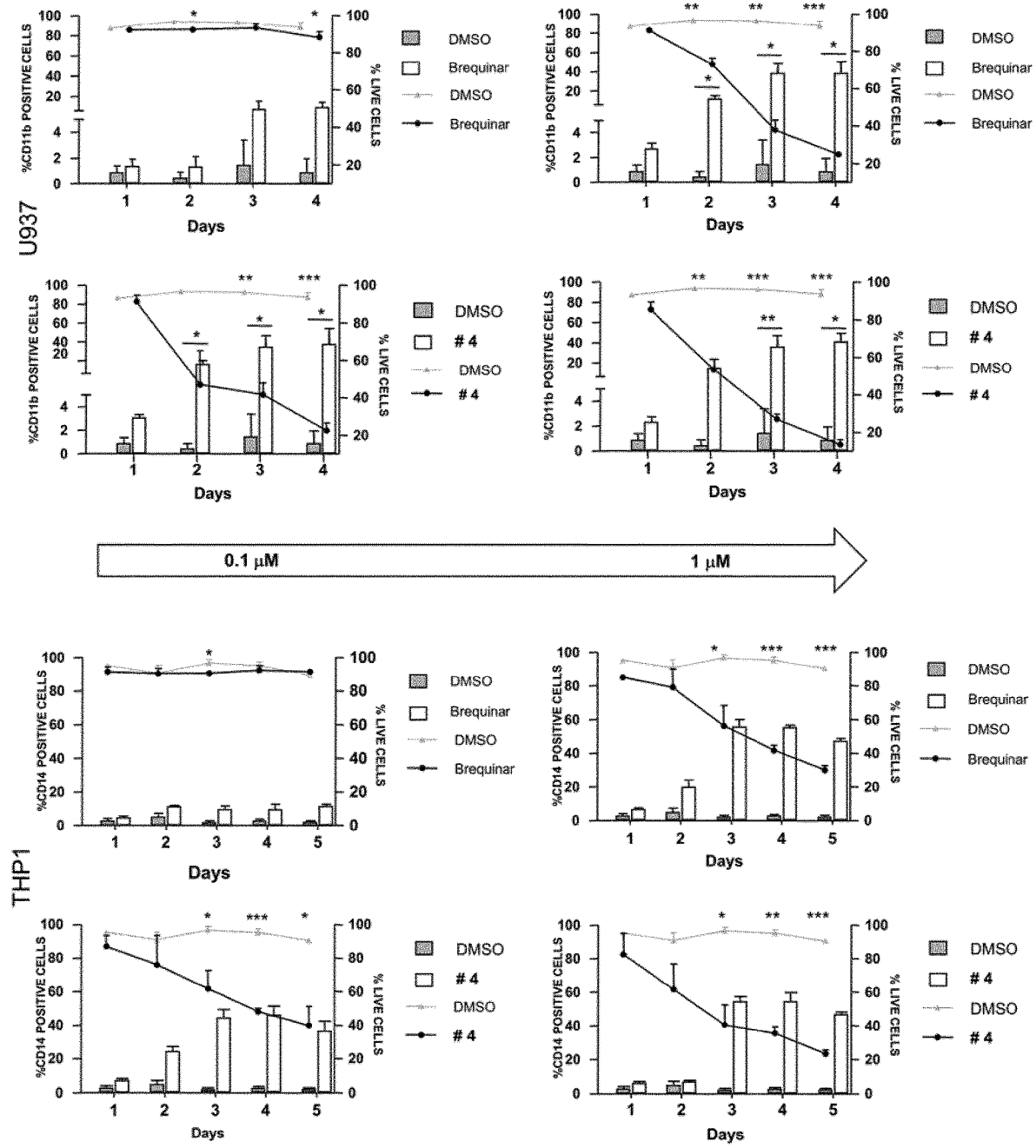
FIG. 7 shows the parallelism between the daily proportion of differentiating cells and cells viability. The proportion of differentiating cells is expressed with bars, and the reference axis is on the left; cells viability is expressed with lines, and the reference axis is on the right. The bottom arrow indicates the concentration of drugs. Experiments were performed both on U937 and THP1 and differentiation was evaluated, respectively, with CD11b and CD14 expression. Statistical significance: *$p<0.05$; $p<0.01$; *$p<0.001$ between treated and untreated cells. DMSO=dimethyl sulfoxide.

In order to further demonstrate the connection between differentiation and hDHODH inhibition, the differentiation experiments were repeated in presence of uridine, and the complete rescue of the phenomenon was observed (FIG. 6C, D). Differentiation experiments had to be stopped after 4 days as differentiated cells progressively died. With this in mind, one can see how compound 4 and brequinar alone caused the death of the vast majority of leukemic cells in vitro, even though the proportion of daily differentiating cells reached a 40% maximum (FIG. 7). Again, compound 4 was able to induce a massive death of leukemic cells already at 0.1 µM, i.e., at a 1-log inferior concentration compared to brequinar.

Cytotoxicity in Different Human Cancer Cell Lines.

In the last phase of their study, the present inventors evaluated the effects of our hDHODH inhibitors on a series of human cancer cell lines. Because representative of different tumour types, they involved five different cell lines, in particular: MDA MB231 (breast cancer cells), A2780 (ovarian cancer cells), PANC-1 (pancreatic cancer cells), HEPG2 (liver hepatocellular cancer cells) and HCT-116 (colon cancer cells). All the experiments were performed on 72 h using initially a cpd 4 concentration range of 0.1-100 µM. In the following it was necessary repeat the test for A2780 e PANC-1 at the concentration range of 1-1000 nM and for HEPG2 and HCT-116 at the concentration range of 1-10000 nM. The results of such experiments can be found in Table 3, brequinar was used as comparison.

TABLE 3

Cytotoxicity of cpd 4 and brequinar in different human cancer cell lines.

| Cell line | Cpd 4 IC$_{50}$ (µM) | Cpd 4 with Uridine IC$_{50}$ (µM) | Brequinar IC$_{50}$ (µM) | Brequinar with Uridine IC$_{50}$ (µM) |
|---|---|---|---|---|
| MDA MB231 | 2.1 | 10.2 | 1.30 | >100 |
| A2780 | <0.1 | 13.9 | <0.1 | 15.5 |
| PANC-1 | <0.1 | <0.1 | 0.28 | <0.1 |
| HEPG2 | 0.028 | >10 | 0.046 | >10 |
| HCT-116 | 0.025 | 4.3 | 0.097 | 3 |

Both cpd 4 and brequinar were founded cytotoxic against all the cell lines they investigated. In each case, the observed citotoxicity was reversed when the experiment was performed in presence of uridine, an indication that the inhibition of hDHODH is behind the observed biological effect. Moving to details, beside the breast cancer line MDA MB231, in all the other cases (A2780, PANC-1, HEPG2 and HCT-116) cpd 4 was found most effective to brequinar, demonstrating a superior drug-like behaviour. The most interesting data can be observed on HEPG2 and HCT-116, liver hepatocellular and colon cancer cells respectively, where cpd 4 presented an IC$_{50}$ in the low nM range.

Physicochemical Characterization and Preliminary ADME Profile

The determination of the main physicochemical properties that govern the ADME profile was carried out for all compounds by measuring their lipophilicity (log $D^{7,4}$), and solubility at physiological pH. Data are reported in Table 4. Compound solubility was evaluated at pH 7.4 in phosphate buffered saline (PBS), at 37° C. to simulate bodily fluid, and in PBS with 2% v/v of DMSO to explore solubility limits under in vitro experimental conditions. Unfortunately, all compounds showed around ten times lower solubility than brequinar. However, the values were sufficient to permit the in vitro tests to be performed. All compounds display good lipophilic-hydrophilic balance, with log D values that are optimal for favorable pharmacokinetic behavior; the difference observed between calculated log P (c log P), and measured log $D^{7,4}$ was in agreement with the presence of significant compound ionization at physiological pH. The serum behavior of compounds 2 and 4, selected for differentiation studies on leukemic cells, was characterized by measuring human serum stability and serum protein binding. Compounds 2 and 4 showed serum profiling that was very similar to that of reference compound brequinar; good stability and a very high percentage of protein binding (Table 5).[28, 29]

TABLE 4

$^{a)}$ clogP calculated using Bio-Loom for Windows, vers.1.5;
$^{b)}$ measured using the shake flask-method. The "n.d." notation indicates that the compound was not tested in that specific assay.

| Compound | Solubility (µM) in PBS | Solubility (µM) in PBS with 2% DMSO | clogP$^a$ | log $D^{7.4}$ ± SD$^b$ |
|---|---|---|---|---|
| Brequinar | 229 | 449 | 6.39 | 1.83 ± 0.02 |
| Teriflunomide | 2692 | n.d. | n.d. | n.d. |
| 2 | 956 | 2169 | 2.59 | 0.98 ± 0.03 |
| 4 | 12 | 27 | 4.06 | 2.35 ± 0.02 |
| 5 | 1.4 | 3.0 | 4.56 | 2.70 ± 0.02 |
| 6 | 2.8 | 0.4 | 4.56 | 2.47 ± 0.09 |
| 8 | 47 | 90 | 4.92 | 2.30 ± 0.02 |
| 9 | 7.0 | 23 | 5.42 | 2.75 ± 0.01 |
| 10 | 2.5 | 27 | 5.27 | 2.93 ± 0.09 |

TABLE 5

Human serum stability and protein binding of compounds 2 and 4, as compared to brequinar.

| Compound | % compound after 24 h in human serum | % bound |
|---|---|---|
| Brequinar | 98 | 98.83 |
| 2 | 86 | 99.51 |
| 4 | 100 | 99.10 |

CONCLUSIONS

The present inventors identified a novel class of inhibitors that are based on hydroxyl-pyrazolo[1,5-a]pyridine, an unusual bioisostere of the carboxylic acid function. Compound 4, one of the most powerful hDHODH inhibitors yet discovered, has clearly been demonstrated to induce myeloid differentiation in two AML cell lines, leading to the massive death of leukemic cells. Notably, this effect was obtained at a concentration that was 1-log lower than that of the lead brequinar, and was restricted to leukemic cells alone. In fact, the inventors have proven that cytotoxicity was not related to hDHODH inhibition per se, as the compound showed little or no toxicity towards Jurkat-T cells, but rather to the differentiation effect exclusively induced in AML cells via hDHODH inhibition. It is therefore apparent that compound 4 displays an optimal toxicity profile and highly selective on-target activity, making it an ideal candidate for further in vivo studies in AML models. Compound 4 was found effective also against other cancer cell lines, in particular on multiple solid tumor lines where the observed $IC_{50}$ was always below 100 nM being on HEPG2 and HCT-116 in the low nM.

Materials and Methods

Chemistry
General Methods.

All chemical reagents were obtained from commercial sources (Sigma Aldrich, Alfa Aesar, FluoroChem), and used without further purification. Thin-layer chromatography (TLC), was carried out to monitor reaction progress. Analytical grade solvents (acetonitrile, diisopropyl ether, diethyl ether, dichloromethane [DCM], dimethylformamide [DMF], ethanol 99.8% v/v, ethyl acetate [EtOAc], hexane, methanol [MeOH], petroleum ether b.p. 40-60° C. [petroleum ether], toluene), were used without further purification. When needed, solvents were dried over 4 Å molecular sieves. Tetrahydrofuran (THF), was distilled from Na and benzophenone under $N_2$ immediately prior to use. Thin layer chromatography (TLC), on silica gel was carried out on 5×20 cm plates at 0.25 mm layer thickness. Anhydrous $MgSO_4$ was used as a drying agent for the organic phases. Compound purification was either achieved using flash column chromatography on silica gel (Merck Kieselgel 60, 230-400 mesh ASTM), and the eluents indicated in the procedures for each compound, or using CombiFlash Rf 200 (Teledyne Isco), with 5-200 mL/min, 200 psi (with automatic injection valve), and RediSep Rf Silica columns (Teledyne Isco), with the eluents indicated in the procedures for each compound. Compounds synthesized in our laboratory generally varied between 90% and 99% purity. Biological experiments were performed on compounds with a purity of at least 95%. Purity was checked using two analytical methods. HPLC analyses were performed on an UHPLC chromatographic system (Perkin Elmer, Flexar). The analytical column was an UHPLC Acquity CSH Fluoro-Phenyl (2.1×100 mm, 1.7 µm particle size, Waters). Compounds were dissolved in acetonitrile and injected through a 20 µl loop. The mobile phase consisted of acetonitrile/water with 0.1% trifluoroacetic acid (ratio between 60/40 and 40/60, depending on the compound's retention factor). UHPLC retention times were obtained at flow rates of 0.5 mL/min, and the column effluent was monitored at 215 and 254 nm, referenced against a 360 nm wavelength. Solubility assays, in PBS at pH 7.4, and stability assays in cell test conditions were performed on a HPLC-UV system (MERK-HITACHI), equipped with an auto sampler of 60 µL injection volume (MERK-HITACHI AS-2000A), a binary HPLC pump (MERK-HITACHI L-6200 IP), and a diode array detector (MERK-HITACHI L-4250). LC analyses were performed using an Agilent Zorbax SB-Phenyl Column (4.6× 250, 5 µm). Melting points (m.p.), were measured on a capillary apparatus (Büchi 540). Final m.p. determination was achieved by placing the sample at a temperature 10° C. below the m.p. and applying a heating rate of 1° C. min-. All compounds were routinely checked by $^1$H- and $^{13}$C-NMR and mass spectrometry. The IR spectra of solid compounds were recorded on FT-IR (PerkinElmer SPECTRUM BXII, KBr dispersions), using the diffuse reflectance apparatus DRIFT ACCY. MS spectra were either performed on a Finnigan-Mat TSQ-700 (70 eV, direct inlet for chemical ionization [CI]), or a Waters Micromass ZQ equipped with an ESCi source for electrospray ionization mass spectra. $^1$H- and $^{13}$C-NMR spectra were either performed on a Bruker Avance 300 instrument or a JEOL ECZR600. The following abbreviations are used for coupling patterns: br=broad, s=singlet, d=doublet, dd=doublet of doublets, t=triplet, q=quartet, m=multiplet. Chemical shifts (δ) are given in parts per million (ppm). In this work protons and carbons are labelled (a, b, c, d, e, f g, h, l, m, n and o) according to Scheme 2. Values marked with an asterisk are interchangeable. Detailed $^{13}$C spectra of tetrafluorinated biphenyl compounds (final compounds 4-7 and intermediates 22a-c), have not been entirely reported due to their especially complicated patterns (attributable to the multiple couplings between fluorine and carbon atoms). For these spectra, only the $^{13}$C signals caused by the heterocyclic substructure and non-aromatic carbons are assigned. For the intermediates 15a, 15b, 15c, 16a, 17a, 18a, 19a, 20a and final compounds 4-6 and 8-10, HRMS spectra were recorded on an LTQ Orbitrap mass spectrometer (Thermo Scientific, Bremen, Germany), equipped with an atmospheric pressure interface and an ESI ion source instrument. Compounds 24[30] and 25[30] were prepared according to previously-described procedures.

General procedures for the synthesis of 15a, 15b, 15c. A solution of hydroxylamine-O-sulfonic acid (HOSA, 18 g, 0.16 mol), and the appropriate type 11 pyridine (3 eq), was stirred in water (150 mL), at 90° C. for 1 h. The solution was cooled to room temperature and $K_2CO_3$ (21.99 g, 0.16 mol), was then added. The resulting suspension was concentrated under vacuum and the residue taken up with abs EtOH (200 mL). The resulting suspension was filtered and diethyl malonate (50.98 g, 48.56 mL, 0.32 mol), was added to the filtrate. The solution was stirred at 90° C. for 3 h and then concentrated under vacuum. The residue was purified via flash chromatography (eluent: dichloromethane/EtOH 9/1 v/v), to afford a brownish sticky oil (type 14), that was used in the subsequent step without any further purification. Potassium tert-butoxide (17.86 g, 1 eq), was added portionwise to a solution of type 14 in dry THF (300 mL). The resulting dark-orange suspension was stirred at room temperature for some minutes until complete conversion was observed, after which it was concentrated under vacuum. The residue was diluted and acidified to pH 2 using 0.5 N HCl (250 mL), and extracted with ethyl acetate (2×150 mL). The organic phases were collected, dried and evaporated under vacuum to afford a yellowish crude oil that was purified by flash chromatography (eluent: dichloromethane/ MeOH 9/1 v/v), to afford the desired compounds as white solids.

Ethyl 2-hydroxypyrazolo[1,5-a]pyridine-3-carboxylate (15a). Pale orange solid (m.p. 150.0 151.3° C., from methanol). Yield 21%. $^1$H-NMR (300 MHz, DMSO): δ 1.29 (t, 3H, J=7.0 Hz, —CH$_2$CH$_3$), 4.24 (q, 2H, J=7.0 Hz, —CH$_2$CH$_3$), 6.98 (t, 1H, J=6.7 Hz, H-b), 7.48 (t, 1H, J=7.5 Hz, H-c), 7.84 (d, 1H, J=8.8 Hz, H-d), 8.55 (d, 1H, J=6.7 Hz, H-a), 11.14 (s, 1H, —OH); $^{13}$C-NMR (75 MHz, DMSO): δ 14.5 (—CH$_2$CH$_3$), 58.9 (—OCH$_2$CH$_3$), 86.4 (C-f), 113.1 (C-b), 116.9 (C-d), 128.2 (C-c), 129.2 (C-a), 141.5 (C-e), 162.7 (C-h)*, 164.5 (C-g)*; MS (CI) 207 (M+1). IR (KBr) ν (cm-1): 3094, 2979, 1700, 1639, 1559, 1534, 1448, 1330, 1246, 1212, 1156, 1107, 1026. ESI-HRMS (m/z) [M+H]+ calcd. for $C_{10}H_{11}N_2O_3$ 207.0764, obsd. 207.0769.

Ethyl 2-hydroxy-7-methyl-pyrazolo[1,5-a]pyridine-3-carboxylate (15b). White solid (m.p. 113.8-114.6° C.; from trituration with diisopropyl ether). Yield 19%. $^1$H-NMR (300 MHz, DMSO): δ 1.30 (t, 3H, J=7.0 Hz, —OCH$_2$CH$_3$), 2.60 (s, 3H, Ar—CH$_3$), 4.24 (q, 2H, J=7.0 Hz, —OCH$_2$CH$_3$), 6.91 (d, 1H, J=6.9 Hz, H-b), 7.42 (t, 1H, J=7.9 Hz, H-c), 7.75 (d, 1H, J=8.7 Hz, H-d), 11.20 (s, 1H, —OH); $^{13}$C-NMR (75 MHz, DMSO): δ 14.5 (—OCH$_2$CH$_3$), 17.4 (Ar—CH$_3$), 58.9 (—OCH$_2$CH$_3$), 86.5 (C-f), 112.67 (C-b), 114.5 (C-d), 128.1 (C-c), 138.3 (C-a), 141.8 (C-e), 162.8 (C-h)*, 164.2 (C-g)*; MS (CI) 221 (M+1). IR (KBr) ν (cm-1): 3069, 2991, 1700, 1637, 1560, 1533, 1385, 1330, 1219, 1163, 1104, 1068, 1039. ESI-HRMS (m/z) [M+H]+ calcd. for C$_{11}$H$_{13}$N$_2$O$_3$ 221.0921, obsd. 221.0926.

Ethyl 2-hydroxy-5-methyl-pyrazolo[1,5-a]pyridine-3-carboxylate (15c). White solid (m.p. 123.4-126.6° C.; from trituration with diisopropyl ether). Yield 19%. $^1$H-NMR (300 MHz, DMSO): δ 1.29 (t, 3H, J=7.1 Hz, —OCH$_2$CH$_3$), 2.37 (s, 3H, Ar—CH$_3$), 4.23 (q, 2H, J=7.1 Hz, —OCH$_2$CH$_3$), 6.82 (dd, 1H, J=6.9, 1.7 Hz, H-b), 7.61 (s, 1H, H-d), 8.42 (d, 1H, J=6.9 Hz, H-a), 11.04 (br s, 1H, —OH); $^{13}$C-NMR (75 MHz, DMSO): δ 14.5 (—OCH$_2$CH$_3$), 21.0 (Ar—CH$_3$), 58.9 (—OCH$_2$CH$_3$), 85.6 (C-f), 115.2 (C-b)*, 115.6 (C-d)*, 128.5 (C-a), 139.1 (C-c), 141.5 (C-e), 162.8 (C-h)*, 164.6 (C-g)*; MS (CI) 221 (M+1). IR (KBr) ν (cm-1): 3064, 2986, 1654, 1561, 1498, 1435, 1305, 1250, 1211, 1185, 1112, 1029. ESI-HRMS (m/z) [M+H]+ calcd. for C$_{11}$H$_{13}$N$_2$O$_3$ 221.0921, obsd. 221.0926.

Ethyl N-benzyl-2-oxo-pyrazolo[1,5-a]pyridine-3-carboxylate (18a) and 4.1.4 ethyl 2-benzyloxypyrazolo[1,5-a]pyridine-3-carboxylate (19a) from 15a. Benzyl bromide (3.0 g, 14.50 mmol), was added dropwise to a mixture of 15a (2.74 g, 16.00 mmol), and cesium carbonate (11.85 g, 36.40 mmol), in dry DMF (50 mL). The reaction mixture was stirred for 18 hours at room temperature and water (100 mL), was then added. The mixture was extracted with EtOAc (3×100 mL), the combined organic layer was washed with brine, and then dried and evaporated under reduced pressure to afford a colorless oil. This latter provided two spots on TLC (eluent: petroleum ether/EtOAc 80/20 v/v), which were ascribed to the two pyrazolo[1,5-a]-pyridine isomers. The mixture was separated using flash chromatography (eluent: petroleum ether/EtOAc 80/20 v/v, then eluent: dichloromethane/MeOH 9:1 v/v). The structures were determined unequivocally using heteronuclear 2D-NMR (HSQC, HMBC and NOESY, see supplementary information).

19a) First isomer eluted, pale yellow solid (m. p: 100.0-100.8° C., from trituration with diisopropyl ether). Yield 75%. $^1$H-NMR (300 MHz DMSO): δ 1.30 (t, 3H, J=7.1 Hz —OCH$_2$CH$_3$), 4.24 (q, 2H, J=7.1 Hz —OCH$_2$CH$_3$), 5.44 (s, 2H, —OCH$_2$Ph), 7.04 (t, 1H, J=6.9 Hz, H-b), 7.29-7.45 (m, 3H, H-o, H-n), 7.47-7.59 (m, 3H, H-m, H-c), 7.91 (d, 1H, J=8.8 Hz, H-d), 8.67 (d, 1H, J=6.8 Hz, H-a); $^{13}$C-NMR (75 MHz DMSO): δ 14.4 (—OCH$_2$CH$_3$), 59.0 (—OCH$_2$CH$_3$), 70.2 (—OCH$_2$Ph), 87.0 (C-f), 113.3 (C-b), 117.2 (C-d), 127.4 (C-m), 127.9 (C-o), 128.3 (C-n), 128.9 (C-c), 129.6 (C-a), 136.6 (C-l), 142.0 (C-e), 161.9 (C-h)*, 164.3 (C-g)*; MS (CI) 297 (M+1). IR (KBr) ν (cm-1): 3097, 3033, 2978, 1675, 1635,1530, 1515, 1440, 1364, 1251, 1208, 1141, 1053, 1021. ESI-HRMS (m/z) [M+H]+ calcd. for C$_{17}$H$_{16}$N$_2$O$_3$ 297.1234, obsd. 297.1240.

18a) Second isomer eluted, white solid (m.p: 172.3-174.0° C., from EtOAc/diisopropyl ether 1/1 v/v). Yield 21%. $^1$H-NMR (300 MHz DMSO): δ 1.28 (t, 3H, J=7.1 Hz —OCH$_2$CH$_3$), 4.22 (q, 2H, J=7.1 Hz —OCH$_2$CH$_3$), 5.43 (s, 2H, —NCH$_2$Ph), 6.95 (td, 1H, J=7.1, 1.0 Hz, H-b), 7.18-7.38 (m, 5H, H-m, H-o, H-n), 7.59 (t, 1H, J=8.0 Hz, H-c), 7.92 (d, 1H, J=8.8 Hz, H-d), 8.41 (d, 1H, J=6.9 Hz, H-a); $^{13}$C-NMR (75 MHz DMSO): δ 14.4 (—OCH$_2$CH$_3$), 44.5 (—NCH$_2$Ph), 59.4 (—OCH$_2$CH$_3$), 84.3 (C-f), 113.3 (C-b), 117.2 (C-d), 126.0 (C-a), 128.0 (C-m), 128.8 (C-o), 129.8 (C-n), 133.3 (C-c), 134.8 (C-1), 143.6 (C-e), 160.8 (C-g)*, 164.0 (C-h)*; MS (CI) 297 (M+1). IR (KBr) ν (cm-1): 3084, 3056, 2977, 1699, 1631, 1547, 1511, 1464, 1431, 1345, 1238, 1135, 1030. ESI-HRMS (m/z) [M+H]+ calcd. for C$_{17}$H$_{16}$N$_2$O$_3$ 297.1234, obsd. 297.1239.

Ethyl N-benzyl-7-methyl-2-oxo-pyrazolo[1,5-a]pyridine-3-carboxylate (18b) and 4.1.6. ethyl 2-benzyloxy-7-methyl-pyrazolo[1,5-a]pyridine-3-carboxylate (19b) from 15b. Benzyl bromide (0.85 g, 4.99 mmol), was added dropwise to a mixture of 15b (1.00 g, 4.54 mmol), and cesium carbonate (3.70 g, 11.35 mmol), in dry DMF (25 mL). The reaction mixture was stirred for 5 hours at room temperature and water (100 mL), was then added. The mixture was extracted using EtOAc (3×100 mL), the combined organic layer was washed with brine, dried and evaporated under reduced pressure to afford a colorless oil. This latter showed two spots on TLC (eluent: petroleum ether/EtOAc 80/20 v/v), ascribed to the two pyrazolo[1,5-a]-pyridine isomers. The mixture was separated using flash chromatography (eluent: petroleum ether/EtOAc 90/10 v/v, then eluent: dichloromethane/MeOH 9:1 v/v). 19b) First isomer eluted, pale yellow solid (m.p. 74.3-75.9° C.; from trituration with diisopropyl ether). Yield 93%. $^1$H-NMR (600 MHz CDCl$_3$): δ 1.41 (t, 3H, J=7.1 Hz —OCH$_2$CH$_3$), 2.68 (s, 3H, Ar—CH$_3$), 4.37 (q, 2H, J=7.1 Hz —OCH$_2$CH$_3$), 5.54 (s, 2H, —OCH$_2$Ph), 6.68 (d, 1H, J=7.0 Hz, H-b), 7.24-7.32 (m, 2H, H-o, H-c), 7.37 (t, 2H, J=7.6 Hz, H-n), 7.58 (d, 2H, J=7.4 Hz, H-m), 7.89 (d, 1H, J=8.8 Hz, H-d); $^{13}$C-NMR (151 MHz CDCl$_3$): δ 14.7 (—OCH$_2$CH$_3$), 17.9 (Ar—CH$_3$), 59.7 (—OCH$_2$CH$_3$), 70.8 (—OCH$_2$Ph), 88.4 (C-f), 112.2 (C-b), 115.7 (C-d), 127.7 (C-m), 127.8 (C-o), 127.9 (C-c), 128.4 (C-n), 137.2 (C-l), 138.9 (C-a), 143.2 (C-e), 163.6 (C-h)*, 164.7 (C-g)*; MS (ESI) 311 (M+1). IR (KBr) ν (cm-1): 3061, 3026, 2974, 1684, 1640,1539, 1516, 1448, 1358, 1274, 1214, 1135, 1107, 1011.

18b) Second isomer eluted, white solid (m.p. 145.0-147.8° C.; from trituration with diisopropyl ether). Yield 5%. $^1$H-NMR (600 MHz DMSO): δ 1.29 (t, 3H, J=7.1 Hz —OCH$_2$CH$_3$), 2.62 (s, 3H. Ar—CH$_3$), 4.22 (q, 2H, J=7.1 Hz, —OCH$_2$CH$_3$), 5.41 (s, 2H, —NCH$_2$Ph), 6.75 (d, 1H, J=7.1 Hz, H-b), 6.96 (d, 2H, J=7.5 Hz, H-m), 7.22 (t, 1H, J=7.2 Hz, H-o), 7.27 (t, 2H, J=7.4 Hz, H-n), 7.53 (t, 1H, J=8.0 Hz, H-c), 7.86 (d, 1H, J=8.7 Hz, H-d); $^{13}$C-NMR (151 MHz DMSO): δ 14.6 (—OCH$_2$CH$_3$), 20.0 (Ar—CH$_3$), 50.4 (—NCH$_2$Ph), 58.9 (—OCH$_2$CH$_3$), 83.8 (C-f), 114.2 (C-b)*, 114.8 (C-d)*, 126.2 (C-m), 127.8 (C-o), 128.9 (C-n), 134.3 (C-c), 135.5 (C-l), 140.3 (C-a), 148.5 (C-e), 163.1 (C-g)*, 165.0 (C-h)*; MS (ESI) 311 (M+1). IR (KBr) ν (cm-1): 2975, 1718, 1647, 1559, 1516, 1437, 1318, 1250, 1154, 1129, 1071.

Ethyl N-benzyl-5-methyl-2-oxo-pyrazolo[1,5-a]pyridine-3-carboxylate (18c) and 4.1.8. ethyl 2-benzyloxy-5-methyl-pyrazolo[1,5-a]pyridine-3-carboxylate (19c) from 15c. Benzyl bromide (0.85 g, 4.99 mmol), was added dropwise to a mixture of 15c (1.00 g, 4.54 mmol), and cesium carbonate (3.70 g, 11.35 mmol), in dry DMF (25 mL). The reaction mixture was stirred for 4 hours at room temperature and water (100 mL), was then added. The mixture was extracted using EtOAc (4×100 mL), the combined organic layer was washed with brine, dried and evaporated under reduced pressure to afford a colorless oil. This latter showed two spots on TLC (eluent: petroleum ether/EtOAc 80/20 v/v), ascribed to the two pyrazolo[1,5-a]-pyridine isomers. The mixture was separated using flash chromatography (eluent: petroleum ether/EtOAc 90/10 v/v, then eluent: dichloromethane/MeOH 9:1 v/v).

19c) First isomer eluted, pale yellow solid (m.p. 81.5-83.0° C.; from trituration with diisopropyl ether). Yield 58%. $^1$H-NMR (600 MHz CDCl$_3$): δ 1.41 (t, 3H, J=7.1 Hz —OCH$_2$CH$_3$), 2.42 (s, 3H, Ar—CH$_3$), 4.37 (q, 2H, J=7.1 Hz —OCH$_2$CH$_3$), 5.48 (s, 2H, —OCH$_2$Ph), 6.66 (dd, 1H, J=6.90 Hz, 1.9 Hz, H-b), 7.31 (t, 1H, J=7.4 Hz, H-o), 7.38 (t, 2H, J=7.6 Hz, H-n), 7.55 (d, 2H, J=7.5 Hz, H-m), 7.79 (s, 1H, H-d), 8.15 (d, 1H, J=6.9 Hz, H-a); $^{13}$C-NMR (151 MHz, CDCl$_3$): δ 14.7 (—OCH$_2$CH$_3$), 21.7 (Ar—CH$_3$), 59.7 (—OCH$_2$CH$_3$), 70.7 (—OCH$_2$Ph), 87.6 (C-f), 115.0 (C-b), 117.1 (C-d), 127.3 (C-m), 127.9 (C-o), 128.1 (C-a), 128.5 (C-n), 136.9 (C-l), 139.3 (C-c), 143.1 (C-e), 163.6 (C-h)*, 165.2 (C-g)*; MS (ESI) 311 (M+1). IR (KBr) ν (cm-1): 3048, 2981, 1687, 1641, 1540, 1519, 1443, 1364, 1289, 1252, 1215, 1172, 1141, 1054.

18c) Second isomer eluted, white solid (m.p. 167.1-169.5° C.; from trituration with diisopropyl ether). Yield 29%. $^1$H-NMR (600 MHz DMSO): δ 1.45 (t, 3H, J=7.1 Hz —OCH$_2$CH$_3$), 3.53 (s, 3H. Ar—CH$_3$), 4.38 (q, 2H, J=7.1 Hz, —OCH$_2$CH$_3$), 5.56 (s, 2H, —NCH$_2$Ph), 6.97 (dd, 1H, J=7.0 Hz, 1.8 HZ, H-b), 7.37 (d, 2H, J=7.3 Hz, H-m ), 7.43 (t, 1H, J=7.3 Hz, H-o), 7.49 (t, 2H, J=7.4 Hz, H-n), 7.90 (s, 1H, H-d), 8.48 (d, 1H, J=7.0 Hz, H-a); $^{13}$C-NMR (151 MHz DMSO): δ 14.6 (—OCH$_2$CH$_3$), 21.1 (Ar—CH$_3$), 43.7 (—NCH$_2$Ph), 58.4 (—OCH$_2$CH$_3$), 82.8 (C-f), 114.4 (C-b), 115.2 (C-d), 124.6 (C-a), 127.2 (C-m), 128.0 (C-o), 128.9 (C-n), 134.1 (C-l), 142.8 (C-c), 144.0 (C-e), 160.4 (C-g)*, 163.3 (C-h)*; MS (ESI) 311 (M+1). IR (KBr) ν (cm-1): 3087, 2979, 1701, 1632, 1539, 1502, 1430, 1365, 1305, 1243, 1160, 1113, 1040.

Ethyl 2-methoxypyrazolo[1,5-a]pyridine-3-carboxylate (16a) and 4.1.10 ethyl 1-methyl-2-oxo-1,2-dihydropyrazolo[1,5-a]pyridine-3-carboxylate (17a) from 15a. Cesium carbonate (1.48 g, 10.67 mmol), was added to a solution of 15a (1.00 g, 4.85 mmol), in dry THF (30 mL), while stirred under nitrogen. Methyl iodide (2.07 g, 7.28 mmol), was then added to the resulting dark orange suspension and the mixture was stirred at 40° C. overnight. The suspension was then concentrated under vacuum, taken up with water (100 mL), and extracted with EtOAc (3×100 mL). The organic layers were collected, dried and evaporated under vacuum to afford a crude material that was purified by flash chromatography, (eluent: petroleum ether/EtOAc 8/2 v/v) and then eluent: dichloromethane/MeOH 9:1 v/v). The structures were determined unequivocally using heteronuclear 2D-NMR (HSQC, HMBC and NOESY, see supplementary information).

16a). White solid (m.p: 128.9-129.4° C., from trituration with diisopropyl ether). Yield 59%. $^1$H-NMR (300 MHz DMSO): δ 1.29 (t, 3H, J=7.1 Hz, —OCH$_2$CH$_3$), 4.00 (s, 3H, —OCH$_3$) 4.23 (q, 2H, J=7.1 Hz, —OCH$_2$CH$_3$), 7.02 (td, 1H, J=6.9 Hz, 1.0 Hz, H-b), 7.52 (t, 1H, J=7.9 Hz, H-c), 7.88 (d, 1H, J=8.9 Hz, H-d), 8.65 (d, 1H, J=6.8 Hz, H-a); $^{13}$C-NMR (75 MHz DMSO): δ 14.5 (—OCH$_2$CH$_3$), 56.5 (—OCH$_3$), 59.0 (—OCH$_2$CH$_3$), 86.7 (C-f), 113.2 (C-b), 117.2 (C-d), 128.8 (C-c), 129.6 (C-a), 142.1 (C-e), 162.0 (C-h)*, 165.0 (C-g)*; MS (CI) 221 (M+1). IR (KBr) ν (cm-1): 3085, 3042, 2990, 1691, 1517, 1449, 1407, 1300, 1245, 1157, 1105, 1023; ESI-HRMS (m/z) [M+H]+ calcd. for C$_{11}$H$_{13}$N$_2$O$_3$ 221.0921, obsd. 221.0924.

17a). Orange solid (m.p. 217.8-224.2° C. dec., from trituration with diisopropyl ether). Yield 35%. $^1$H-NMR (300 MHz DMSO): δ 1.28 (t, 3H, J=7.0 Hz, —OCH$_2$CH$_3$), 3.58 (s, 3H, —NCH$_3$), 4.21 (q, 2H, J=7.0 Hz —OCH$_2$CH$_3$), 7.10 (t, 1H, J=6.6 Hz, H-b), 7.66 (t, 1H, J=7.8 Hz, H-c), 7.90 (d, 1H, J=8.6 Hz, H-d), 8.57 (d, 1H, J=6.3 Hz, H-a); $^{13}$C-NMR (75 MHz DMSO): δ 14.5 (—CH$_2$CH$_3$), 28.9 (—NCH$_3$), 59.3 (—CH$_2$CH$_3$), 84.2 (C-f), 113.3 (C-b), 116.7 (C-d), 125.8 (C-a), 132.9 (C-c), 142.6 (C-e), 160.6 (C-g), 164.1 (C-h); MS(CI) 221 (M+1). IR (KBr) ν (cm-1): 3507, 3069, 3025, 2977, 1687, 1625, 1511, 1477, 1437, 1256, 1227, 1189, 1093, 1024; ESI-HRMS (m/z) [M+H]+ calcd. for C$_{11}$H$_{13}$N$_2$O$_3$ 221.0921, obsd. 221.0925.

General procedure for base-catalyzed ester hydrolysis (20a-c). 5M NaOH (5 eq.), was added to a solution of the appropriate ester in ethanol. The solution was stirred for 5 hours at 70° C., then neutralized with 6M HCl and concentrated under reduced pressure. 2M HCl was added at 0° C. until pH 2 was reached and the resulting suspension was filtered to afford the corresponding acid.

2-Benzyloxypyrazolo[1,5-a]pyridine-3-carboxylic acid (20a). Obtained from 19a. White solid (m.p. 159.9-160.5° C.; from trituration with diisopropyl ether). Yield 99%. $^1$H-NMR (300 MHz DMSO): δ 5.43 (s, 2H, —OCH$_2$Ph), 7.01 (t, 1H, J=6.50 Hz H-b), 7.28-7.45 (m, 3H, H-o, H-n), 7.46-7.57 (m, 3H, H-m, H-c), 7.93 (d, 1H, J=8.80 Hz, H-d), 8.65 (d, 1H, J=6.80 Hz, H-a), 12.10 (s, 1H, , COOH); $^{13}$C-NMR (75 MHz, DMSO): δ 71.1 (—OCH$_2$Ph), 88.4 (C-f), 114.0 (C-b), 118.2 (C-d), 128.6 (C-m), 128.8 (C-o), 129.2 (C-n), 129.3 (C-c), 130.3 (C-a), 137.5 (C-l), 143.2 (C-e), 164.3 (C-g)*, 165.2 (C-h)*; MS(CI) 225 (M-CO$_2$+1); IR (KBr) ν (cm-1): 2894, 2650, 1654, 1628, 1527, 1508, 1477, 1454, 1438, 1371, 1332, 1302, 1258, 1211, 1183, 1133, 1080, 1006; ESI-HRMS (m/z) [M+H]+ calcd. for C$_{15}$H$_{13}$N$_2$O$_3$ 269.0921, obsd. 269.0926.

2-Benzyloxy-7-methyl-pyrazolo[1,5-a]pyridine-3-carboxylic acid (20b). Obtained from 19b. White solid (m.p. 181.1-181.8° C.; from trituration with diisopropyl ether). Yield 72%. $^1$H-NMR (600 MHz DMSO): δ 2.65 (s, 3H, Ar—CH$_3$), 5.46 (s, 2H, —OCH$_2$Ph), 6.94 (d, 1H, J=7.0 Hz, H-b), 7.34 (t, 1H, J=7.3 Hz, H-c), 7.40 (t, 2H, J=7.5 Hz, H-n), 7.44 (t, 1H, J=8.0 Hz, H-o), 7.55 (d, 2H, J=7.3 Hz H-m), 7.83 (d, 1H, J=8.7 Hz, H-d), 12.10 (s, 1H, COOH); $^{13}$C-NMR (151 MHz, DMSO): δ 17.8 (Ar—CH$_3$), 70.7 (—OCH$_2$Ph), 88.2 (C-f), 113.0 (C-b), 115.5 (C-d), 128.5 (C-o), 128.6 (C-m), 128.9 (C-n), 128.9 (C-c), 137.2 (C-l), 139.1 (C-a), 143.2 (C-e), 164.2 (C-g)*, 164.4 (C-h)*; MS (ESI) 283 (M+1). IR (KBr) ν (cm-1):3030, 2632, 1657, 1632, 1560, 1509, 1450, 1364, 1286, 1215, 1154, 1129, 1062, 1007, 962.

2-Benzyloxy-5-methyl-pyrazolo[1,5-a]pyridine-3-carboxylic acid (20c). Obtained from 19c. White solid (m.p. 174.3-174.9° C.; from trituration with diisopropyl ether). Yield 96%. $^1$H-NMR (600 MHz DMSO): δ 2.39 (s, 3H, Ar—CH$_3$), 5.40 (s, 2H, —OCH$_2$Ph), 6.85 (d, 1H, J=6.9 Hz, H-b), 7.34 (t, 1H, J=7.3 Hz, H-o), 7.40 (t, 2H, J=7.5 Hz, H-n), 7.50 (d, 2H, J=7.4 Hz, H-m), 7.71 (s, 1H, H-d), 8.52 (d, 1H, J=6.9 Hz, H-a), 12.01 (s, 1H, COOH); $^{13}$C-NMR (151 MHz, DMSO): δ 21.0 (Ar—CH$_3$), 70.1 (—OCH$_2$Ph), 86.7 (C-f), 115.3 (C-b)*, 116.0 (C-d)*, 127.8 (C-m), 128.0 (C-o), 128.4 (C-n), 128.8 (C-a), 136.7 (C-l), 139.5 (C-c), 142.4 (C-e), 163.6 (C-h)*, 164.5 (C-g)*; MS (ESI) 283 (M+1). IR (KBr) ν (cm-1): 2887, 2629, 1662, 1632, 1534, 1507, 1458, 1357, 1312, 1254, 1206, 1140, 1116, 1033, 997, 962.

General procedure for synthesis of pyrazolo[1,5-a]pyridine related amides 26-28. 2M oxalyl chloride in dry dichloromethane (1.75 mL, 3.50 mmol), and dry DMF (1 drop), were added to a cooled (0° C.), solution of 20a (1.00 mmol), in dry THF (15 mL), under a nitrogen atmosphere. The reaction mixture was stirred for 2 hours at room temperature under a nitrogen atmosphere. The solution was concentrated under reduced pressure and the residue was dissolved in dry THF (10 mL, this step was repeated three times). The resulting acyl chloride was dissolved in dry toluene (15 mL). A solution of the appropriate aniline (1.00 mmol), and dry pyridine (3.00 mmol), in dry toluene (5 mL), was added dropwise to the solution of acyl chloride under nitrogen atmosphere. The resulting mixture was stirred at reflux overnight, then cooled to room temperature and quenched with 0.5M HCl (25 mL). The layers were resolved, the aqueous phase was further extracted with EtOAc (3×50 mL), and the combined organic layer was washed with brine, dried and evaporated under reduced pressure. The crude material was purified using flash chromatography.

2-Benzyloxy-N-(4-phenoxyphenyl)pyrazolo[1,5-a]pyridine-3-carboxamide (26). Obtained from 20a, using aniline 23. Flash chromatography (eluent: dichloromethane/EtOAc 98:2 v/v). White solid (m.p. 170.6-171.3° C.; from trituration with diisopropyl ether). Yield 810%. $^1$H-NMR (300 MHz, CDCl$_3$): 95.52 (s, 2H, —OCH$_2$Ph), 6.80 (td, 1H, J=6.9 Hz, 1.5 Hz, H-b), 6.90 (d, 4H, J=8.8 Hz, aromatic protons), 6.99 (t, 1H, J=7.4 Hz, aromatic proton), 7.16-7.53 (m, 11H, aromatic protons), 8.23 (d, 2H, J=8.5 Hz, aromatic protons), 8.62 (s, 1H, —NH); $^{13}$C-NMR (151 MHz CDCl$_3$): 972.2 (—OCH$_2$Ph), 90.9 (C-f), 112.9 (C-b), 118.3, 118.9 (C-d), 120.0, 121.2, 122.9, 127.7 (C-c), 128.3, 128.7, 128.9 (C-a)*, 129.0, 129.8, 134.5, 135.8, 143.0, 152.7, 158.0, 161.2 (C-h)*, 162.2 (C-g)*; MS (ESI) 450 (M+1). IR (KBr) ν (cm$^{-1}$): 3379, 3059, 3039, 1661, 1636, 1545, 1532, 1487, 1464, 1364, 1307, 1223, 1150, 1127, 1103, 1010.

2-Benzyloxy-N-(2-methyl-4-phenoxy-phenyl)pyrazolo[1,5-a]pyridine-3-carboxamide (27). Obtained from 20a, using aniline 24. Flash chromatography eluent: dichloromethane /EtOAc 98:2 v/v). Brown solid (m.p. 172.0-173.0° C.; from trituration with diisopropyl ether). Yield 97%. $^1$H-NMR (600 MHz, CDCl$_3$): δ 2.19 (s, 3H, Ar—CH$_3$), 5.57 (s, 2H, —OCH$_2$Ph), 6.85-6.89 (m, 4H, aromatic protons), 7.01 (t, 1H, J=7.5 Hz, aromatic protons), 7.24-7.30 (m, 3H, aromatic protons), 7.35-7.49 (m, 5H, aromatic protons), 7.54-7.58 (m, 2H, aromatic protons), 8.29-8.33 (m, 2H, aromatic protons), 8.69 (s, 1H, —NH); $^{13}$C-NMR (151 MHz CDCl$_3$): 316.4 (Ar—CH$_3$), 72.2 (—OCH$_2$Ph), 90.9 (C-f), 112.8, 116.7, 118.4, 118.9, 120.9, 122.1, 122.6, 127.6, 128.2, 128.6, 128.9, 129.0, 129.7, 131.0, 135.0, 143.0 (C-e), 149.9, 158.5, 161.2 (C-h)*, 162.2 (C-g)*; MS (ESI) 450 (M+1). IR (KBr) ν (cm$^{-1}$): 3382, 3059, 3042, 1655, 1637, 1557, 1548, 1534, 1489, 1458, 1406, 1337, 1291,1250,1223, 1146, 1117, 997.

2-Benzyloxy-N-(2,5-dimethyl-4-phenoxy-phenyl)pyrazolo[1,5-a]pyridine-3-carboxamide (28). Obtained from 20a, using aniline 25. Flash chromatography eluent: dichloromethane /EtOAc 98:2 v/v). Brown solid (m.p. 212.8-213.6° C.; from trituration with diisopropyl ether). Yield 98%. $^1$H-NMR (600 MHz, CDCl$_3$): 91.77 (s, 3H, Ar—CH$_3$), 2.18 (s, 3H, Ar—CH$_3$), 5.52 (s, 2H, —OCH$_2$Ph), 6.66 (s, 1H, aromatic proton), 6.82-6.90 (m, 3H, aromatic protons), 6.98 (t, 1H, J=7.5 Hz, aromatic protons), 7.22-7.27 (m, 2H, aromatic protons), 7.34-7.43 (m, 4H, aromatic protons), 7.49-7.54 (m, 2H, aromatic protons), 8.17 (s, 1H, aromatic proton); 8.29-8.36 (m, 2H, aromatic protons), 8.42 (s, 1H, —NH); $^{13}$C-NMR (151 MHz CDCl$_3$): 916.2 (Ar—CH$_3$), 17.1 (Ar—CH$_3$), 72.6 (—OCH$_2$Ph), 91.1, 112.8, 116.8, 119.0, 122.0, 122.1, 124.4, 126.6, 127.6, 128.4, 128.7, 128.9, 129.2, 129.4, 129.7, 133.2, 135.4, 143.1 (C-e), 149.8, 158.6, 161.2 (C-h)*, 162.2 (C-g)*; MS (ESI) 464 (M+1). IR (KBr) ν (cm$^{-1}$): 3392, 3059, 3044, 2923, 2854, 1658, 1638, 1586, 1532, 1486, 1462, 1402, 1361, 1292, 1223, 1148, 1079, 1000.

2-(Benzyloxy)-N-(2-isopropyl-5-methyl-4-phenoxyphenyl)pyrazolo[1,5-a]pyridine-3-carboxamide (35). Obtained from 20a, using aniline 34. Flash chromatography eluent: petroleum ether/ethyl acetate 70/30 v/v). White solid (m.p. 166.2-167.7° C.; from trituration with diisopropyl ether) Yield 55%. $^1$H NMR (600 MHz, CDCl$_3$): δ 0.84 (d, 6H, J=6.8 Hz, CH(CH$_3$)$_2$), 2.09 (s, 3H, —CH$_3$), 2.66 (hept, 1H, J=6.7 Hz, —CH(CH$_3$)$_2$), 5.48 (s, 2H, —OCH$_2$Ph), 6.74 (s, 1H, aromatic proton), 6.78 (d, 2H, J=8.0 Hz, aromatic protons), 6.80 (t, 1H, J=6.9 Hz, H-b), 6.91 (t, 1H, J=7.3 Hz, aromatic proton), 7.18 (t, 2H, J=7.9 Hz, aromatic protons), 7.36-7.29 (m, 4H, aromatic protons), 7.46 (d, 2H, J=6.6 Hz, aromatic protons), 7.95 (s, 1H, aromatic proton), 8.25 (d, 1H, J=6.8 Hz, H-a), 8.29 (d, 1H, J=8.8 Hz, H-d), 8.42 (s, 1H, —NH). $^{13}$C NMR (151 MHz, CDCl$_3$): δ 16.1 (—CH$_3$), 22.7 CH(CH$_3$)$_2$), 27.8 (—CH(CH$_3$)$_2$), 72.5 (—OCH$_2$Ph), 91.0 (C-f), 112.8 (C-b), 116.3, 117.9, 119.0 (C-d), 121.8, 126.4, 127.6 (C-c), 128.3, 128.6, 129.0 (C-a), 129.1, 129.2, 129.6, 131.4, 135.5, 138.4, 143.2, 150.3, 158.7, 161.5 (C-h)*, 162.4 (C-g)*; IR (KBr) ν (cm-1): 3398, 3040,2963, 1652, 1636, 1528, 1490, 1445, 1402,1368,1289,1220,1181,1147, 1127,1044, 993; MS (ESI) 492 (M+1).

General procedure for the synthesis of pyrazolo[1,5-a] pyridine related amides 22a-c. 2M Oxalyl chloride in dry dichloromethane (3.0 mmol), and dry DMF (1 drop), were added to a cooled (0° C.), solution of the related pyrazolo [1,5-a]pyridine acid (1.0 mmol) 20a-c, in dry THF (20 mL), under a nitrogen atmosphere. The obtained solution was stirred at room temperature for 2 hours. The solution was then concentrated under reduced pressure and the residue dissolved in dry THF (10 mL, this step was repeated three times). The resulting acyl chloride was immediately used without any further purification. Trimethylaluminium (2.0 M in hexane, 1.5 mmol), was added to a solution of the 2,3,5,6-tetrafluoro-4-phenylaniline 21 (1.1 mmol), in dry toluene (15 mL), under a nitrogen atmosphere. The resulting mixture was stirred for 2 hours at room temperature producing a brown suspension which was then quantitatively portionwise transferred to a solution of a previously-described acyl chloride in dry toluene (30 mL). The mixture was heated overnight at 90° C. and then cooled to r.t. The reaction was quenched with 1M HCl. The layers were resolved and the aqueous phase was exhaustively extracted using EtOAc. The combined organic layer was washed with 1M NaOH and brine, dried and the solvent was evaporated under reduced pressure. The crude product was purified by column chromatography.

1-Benzyl-2-oxo-N-(2,3,5,6-tetrafluoro-[1,1'-biphenyl]-4-yl)-1,2-dihydropyrazolo[1,5-a]pyridine-3-carboxamide (22a). Obtained from 20a, flash chromatography (eluent: petroleum ether/EtOAc 90:10 v/v). Pale yellow solid (m.p. 223.8-225.9° C.; from trituration with diisopropyl ether). Yield 45%. $^1$H NMR (300 MHz, CDCl$_3$): δ 5.48 (s 2H, —NCH$_2$Ph), 6.76 (t, 1H, J=7.0 Hz, H-b), 7.19-7.58 (m, 11H, aromatic protons and H-c), 7.73 (d, 1H, J=7.0 Hz, H-d), 8.28 (d, 1H, J=8.8 Hz, H-a), 9.98 (s, 1H, —NH); $^{13}$C NMR (75 MHz, CDCl$_3$): δ 45.6 (—NCH$_2$Ph), 87.1 (C-f), 112.9 (C-b), 118.3 (C-d), 123.0 (C-a), 127.1, 128.7, 128.9, 129.1, 129.6, 130.3, 131.8, 132.5, 142.5, 161.7 (C-g)*, 162.1 (C-h)*; MS (ESI) 492 (M+1). IR (KBr) ν (cm$^{-1}$): 3227, 3101, 3063, 1667, 1628, 1519, 1484, 1438, 1313, 1239, 1172, 1152, 1113, 1076, 1004, 972.

1-Benzyl-7-methyl-2-oxo-N-(2,3,5,6-tetrafluoro-[1,1'-biphenyl]-4-yl)-1,2-dihydropyrazolo[1,5-a]pyridine-3-carboxamide (22b). Obtained from 20b, flash chromatography (eluent: petroleum ether/EtOAc 95:5 v/v). Pale yellow solid (m.p. 220.8-222.3° C.; from trituration with diisopropyl ether). Yield 41%. $^1$H NMR (600 MHz, CDCl$_3$): δ 2.67 (s, 3H, Ar—CH$_3$), 5.58 (s, 2H, —NCH$_2$Ph), 6.51 (d, 1H, J=7.1

Hz, H-b), 6.94 (d, 2H, J=6.7, H-m), 7.23-7.31 (m, 3H, H-n, H-o), 7.38 (dd, 1H, J=8.8 Hz, 7.2 Hz, H-c), 7.43-7.53 (m, 5H, aromatic protons), 8.25 (d, 1H, J=8.50 Hz, H-d), 10.07 (s, 1H, —NH); $^{13}$C NMR (151 MHz, CDCl$_3$): δ 20.7 (Ar—CH$_3$), 51.8 (—NCH$_2$Ph), 87.5 (C-f), 115.2 (C-b)*, 116.3 (C-d)*, 117.7, 126.1, 127.7, 128.5, 128.7, 129.1, 129.4, 130.4, 133.7 (C-c), 134.5 (C-l), 137.0, 138.9 (C-a), 143.3, 143.7, 148.2, 161.8 (C-g)*, 167.5 (C-h)*; MS (ESI) 506 (M+1). IR (KBr) ν (cm$^{-1}$): 3231, 3160, 3100, 3027, 2925, 1688, 1626, 1604, 1560, 1532, 1483, 1451, 1424, 1312, 1256, 1182, 1160, 1139, 1102, 1009, 982.

1-Benzyl-5-methyl-2-oxo-N-(2,3,5,6-tetrafluoro-[1,1'-biphenyl]-4-yl)-1,2-dihydropyrazolo[1,5-a]pyridine-3-carboxamide (22c). Obtained from 20c, flash chromatography (eluent: petroleum ether/EtOAc 90:10 v/v). Pale yellow solid (m.p. 200.7-202.7° C.; from trituration with diisopropyl ether). Yield 38%. $^1$H NMR (600 MHz, CDCl$_3$): 92.38 (s, 3H, Ar—CH$_3$), 5.44 (s, 2H, —NCH$_2$Ph), 6.57 (dd, 1H, J=7.1 Hz, 1.7 Hz, H-b), 7.27 (d, 2H, J=6.9, H-m), 7.34 (t, 1H, J=7.3 Hz, H-o), 7.38 (t, 2H, J=7.3 Hz, H-n), 7.43-7.53 (m, 5H, aromatic protons), 7.58 (d, 1H, J=7.1 Hz, H-a), 8.11 (s, 1H, H-d), 10.07 (s, 1H, —NH); $^{13}$C NMR (151 MHz, CDCl$_3$): 321.6 (Ar—CH$_3$), 45.6 (—NCH$_2$Ph), 86.3 (C-f), 115.0 (C-b), 116.3, 117.3 (C-d), 117.5, 122.3 (C-a), 127.0, 127.7, 128.6, 128.8, 129.0, 129.6, 130.3, 132.8 (C-l), 142.5 (C-c), 143.4, 143.6, 144.0 (C-e), 161.8 (C-g)*, 162.6 (C-h)*; MS (ESI) 506 (M+1). IR (KBr) ν (cm$^{-1}$): 3233, 3101, 3066, 1672, 1653, 1631, 1528, 1487, 1438, 1311, 1242, 1176, 1126, 1076, 977.

1-Benzyl-2-oxo-N-(2,3,3',5,6-pentafluoro-[1,1'-biphenyl]-4-yl)-1,2-dihydropyrazolo[1,5-a]pyridine-3-carboxamide (36b). Obtained from 20a, flash chromatography (eluent: from petroleum ether/L EtOAc 80:20 v/v to 5:5 v/v). White solid. Yield 40%. $^1$H NMR (600 MHz, DMSO): 35.53 (s, 2H, —NCH$_2$Ph), 7.04 (td, 1H, J=7.1, 1.3 Hz, H-b), 7.24-7.37 (m, 6H, aromatic protons), 7.38 (d, 1H, J=7.7 Hz, aromatic proton), 7.46 (d, 1H, J=9.5 Hz, aromatic proton), 7.58 (td, 1H, J=8.0, 6.4 Hz, aromatic proton), 7.65 (t, 1H, J=7.9 Hz, H-c), 8.01 (d, 1H, J=8.7 Hz, H-d), 8.49 (d, 1H, J=7.0, H-a), 10.08 (s, 1H, —NH); $^{13}$C NMR (151 MHz, CDCl$_3$): 944.2 (—NCH$_2$Ph), 85.4 (C-f), 113.3 (C-b), 115.4 (t, J=17.3 Hz), 116.2 (C-d), 116.4 (d, J=20.8 Hz), 117.1, 117.2 (d, J=23.1 Hz), 125.2, 126.5, 127.2, 128.2, 128.8 (d, J=9.8 Hz), 129.1, 130.9 (d, J=8.4 Hz), 132.9, 133.7, 142.4, 142.8, 144.1, 160.6 (C-g)*, 161.7 (C-h)*. 162.0 (d, J=244.3 Hz); MS (ESI) 508 (M−1).

1-Benzyl-2-oxo-N-(2,3,5,6-tetrafluoro-3'-(trifluoromethyl)-[1,1'-biphenyl]-4-yl)-1,2-dihydropyrazolo[1,5-a]pyridine-3-carboxamide (36c). Obtained from 20a, flash chromatography (eluent: from petroleum ether/EtOAc 80:20 v/v to 5:5 v/v). White solid. Yield 40%. $^1$H NMR (600 MHz, CDCl$_3$): 95.49 (s, 2H, —NCH$_2$Ph), 6.78 (t, 1H, J=6.8 Hz, H-b), 7.29 (d, 2H, J=7.3 Hz, aromatic protons), 7.36 (t, 1H, J=7.2 Hz, aromatic proton), 7.38-7.42 (m, 2H, aromatic protons), 7.48 (t, 1H, J=7.9 Hz, H-c), 7.64 (t, 1H, J=7.7 Hz, aromatic protons), 7.68 (d, 1H, J=7.5 Hz, aromatic protons), 7.72 (t, 2H, J=7.6 Hz), 7.76 (s, 1H, aromatic proton), 8.31 (d, 1H, J=8.8, H-d), 10.08 (s, 1H, —NH); $^{13}$C NMR (151 MHz, CDCl$_3$): δ45.7 (—NCH$_2$Ph), 87.2 (C-f), 112.9 (C-b), 116.4 (t, J=17.3 Hz), 117.2 (t, J=12.2 Hz), 118.5 (C-d), 123.0, 124.0 (q, J=272.1 Hz), 125.9 (q, J=3.9 Hz), 127.1, 127.2, 128.5, 129.0, 129.3, 129.7, 131.3 (q, J=32.4 Hz), 131.8, 132.5, 133.7, 142.7, 142.9, 144.1, 161.6 (C-g)*, 162.2 (C-h)*; MS (ESI) 560 (M+1).

1-Methyl-2-oxo-N-(2,3,5,6-tetrafluoro-[1,1'-biphenyl]-4-yl)-1,2-dihydropyrazolo[1,5-a]pyridine-3-carboxamide (7). 5M NaOH (1 eq.), was added to a solution of compound 17a (600 mg, 2.73 mmol), in ethanol (20 mL). The solution was stirred for 3 hours at 70° C., then concentrated under reduced pressure to afford, in a quantitative yield, the corresponding acid sodium salt 17b, which was used in the next step, after dehydration, without further purification. 2M Oxalyl chloride in dry DCM (2.45 mL, 4.90 mmol), and dry DMF (1 drop), were added to a cooled (0° C.), solution of 17b (350 mg, 1.63 mmol), in dry THF (25 mL), under a nitrogen atmosphere and the resulting solution was stirred at room temperature for 2 hours. The solution was then concentrated under reduced pressure and the residue dissolved in dry THF (10 mL, this step was repeated three times), giving the corresponding acyl chloride, which was immediately used without any further purification. Trimethylaluminium (2.0 M in hexane, 1.86 mL, 3.72 mmol), was added to a solution of 2,3,5,6-tetrafluoro-4-phenylaniline 21 (394 mg, 1.96 mmol), in dry toluene (15 mL), under a nitrogen atmosphere. The resulting mixture was stirred for 2 hours at room temperature resulting in a brown suspension, which was quantitatively transferred portionwise to a solution of acyl chloride, raised from the previous steps, in dry toluene (30 mL). The mixture was heated overnight at 90° C., cooled to r.t. and then quenched with 1M HCl. The layers were resolved and the aqueous phase exhaustively extracted with ethyl acetate. The combined organic layer was washed with 1M NaOH and brine, dried and the solvent was evaporated under reduced pressure. The crude product was purified by column chromatography (petroleum ether/EtOAc from 8:2 to 6:4 v/v), to afford the title compound as a pale yellow solid. Yield 27%. $^1$H NMR (300 MHz, DMSO): δ 3.70 (s, 3H, —NCH$_3$), 7.22 (t, 1H, J=6.5, H-b), 7.46-7.63 (m, 5H, aromatic protons), 7.76 (t, 1H, J=7.9, H-c), 8.06 (d, 1H, J=8.7 Hz, H-d), 8.73 (d, 1H, J=6.9 Hz, H-a), 10.10 (s, 1H, —NH); $^{13}$C NMR (75 MHz, DMSO): δ28.5 (—NCH$_3$), 85.8 (C-f), 113.3 (C-b), 116.1 (C-d), 117.1, 125.2 (C-a), 127.1, 129.1, 129.6, 130.4, 132.5, 140.9, 141.1, 144.2, 144.4, 161.2 (C-g)*, 161.8 (C-h)*; MS (ESI) 416 (M+1).

General hydrogenation procedure for target compounds 8-10, 29. Palladium on carbon (Pd/C, 45 mg), was added to a solution of the appropriate amide (compounds 26-28, 0.300 mmol), in dry THF (15 mL). The resulting mixture was vigorously stirred under a hydrogen atmosphere for 3 hours. The suspension was filtered through Celite and the cake was washed with methanol. The filtrate was concentrated under reduced pressure. When necessary, the obtained solid was further purified by flash chromatography.

2-Hydroxy-N-(4-phenoxyphenyl)pyrazolo[1,5-a]pyridine-3-carboxamide (8). Obtained from 26, flash chromatography (eluent: dichloromethane/EtOAc/HCOOH 85:15:1 v/v/v). Brown solid (m.p. 147.6-148.2° C.; from trituration with diisopropyl ether). Yield 80%. $^1$H-NMR (600 MHz, DMSO): δ6.91-7.05 (m, 5H, aromatic protons), 7.10 (t, 1H, J=7.3 Hz, H-b), 7.37 (t, 2H, J=7.9 Hz, aromatic protons), 7.46 (t, 1H, J=7.9 Hz, H-c), 7.70 (d, 2H, J=8.9 Hz, aromatic protons), 8.05 (d, 1H, J=8.7 Hz, H-d), 8.56 (d, 1H, J=6.8 Hz, H-a), 9.05 (s, 1H, —NH), 12.77 (br s, 1H, —OH); $^{13}$C-NMR (151 MHz DMSO): δ89.3 (C-f), 112.7 (C-b), 117.0 (C-d), 117.9, 119.5, 121.0, 122.9, 127.6 (C-c), 128.9 (C-a), 129.9, 134.7, 141.5 (C-e), 151.6, 157.4, 160.8 (C-h)*, 161.9 (C-g)*; MS (ESI) 346 (M+1). IR (KBr) ν (cm$^{-1}$): 3370, 3036, 2571, 1661, 1602, 1544, 1505, 1490, 1449, 1335, 1260, 1231, 1124, 1103, 983. ESI-HRMS (m/z) [M+H]+ calcd. for C$_{20}$H$_{16}$N$_3$O$_3$ 346.1186, obsd. 346.1184.

2-Hydroxy-N-(3-methyl-4-phenoxyphenyl)pyrazolo[1,5-a]pyridine-3-carboxamide (9). Obtained from 27, flash chromatography (eluent: dichloromethane/EtOAc/HCOOH 80:20:1 v/v/v). Brown solid (m.p. 233.7-235.9° C. dec.;

from trituration with diisopropyl ether). Yield 85%. ¹H-NMR (600 MHz, DMSO): δ2.14 (s, 3H, Ar—CH₃), 6.83-6.94 (m, 3H, aromatic protons), 6.98 (td, 1H, J=7.0 Hz, 1.3 Hz, H-b), 7.04 (t, 1H, J=7.4 Hz, aromatic proton), 7.33 (dd, 2H, J=8.4 Hz, 7.6 Hz, aromatic protons), 7.47 (t, 1H, J=7.9 Hz, H-c), 7.56 (dd, 1H, J=8.7 Hz, 2.5 Hz, aromatic proton), 7.63 (d, 1H, J=2.2 Hz, aromatic proton), 8.06 (d, 1H, J=8.7 Hz, H-d), 8.57 (d, 1H, J=6.8 Hz, H-a), 9.04 (s, 1H, —NH), 12.82 (br s, 1H, —OH); ¹³C-NMR (151 MHz DMSO): δ 16.8 (Ar—CH₃), 90.2 (C-f), 113.7 (C-b), 117.2, 117.9 (C-d), 119.3, 121.5, 123.0, 123.1, 128.6 (C-c), 129.8 (C-a), 130.7, 130.8, 136.2, 142.4 (C-e), 149.7, 158.8, 161.7 (C-h)*, 162.8 (C-g)*; MS (ESI) 360 (M+1). IR (KBr) ν (cm-1):3387, 3061, 2572, 1666, 1638, 1534, 1488, 1328, 1226, 1130, 1107, 932. ESI-HRMS (m/z) [M+H]+ calcd. for $C_{21}H_{18}N_3O_3$ 360.1343, obsd. 360.1337.

N-(2,5-Dimethyl-4-phenoxyphenyl)-2-hydroxypyrazolo[1,5-a]pyridine-3-carboxamide (10). Obtained from 28, flash chromatography (eluent: dichloromethane/EtOAc/HCOOH 80:20:1 v/v/v). Brown solid (m.p. 249.1-254.2° C. dec.; from trituration with diisopropyl ether). Yield 67%. ¹H-NMR (600 MHz, DMSO): δ2.12 (s, 3H, Ar—CH₃), 2.24 (s, 3H, Ar—CH₃), 6.73-7.10 (m, 5H, aromatic protons, H-b)), 7.33 (t, 2H, J=7.7 Hz, aromatic protons), 7.48 (t, 1H, J=7.4 Hz, aromatic proton), 7.33 (dd, 2H, J=8.4 Hz, 7.6 Hz, aromatic protons), 7.48 (t, 1H, J=7.8 Hz, H-c), 8.08 (d, 1H, J=8.7 Hz, H-d), 8.19 (s, 1H, aromatic proton), 8.58 (d, 1H, J=6.6 Hz, H-a), 9.04 (s, 1H, —NH), 13.00 (br s, 1H, —OH); ¹³C-NMR (151 MHz DMSO): 916.7 (Ar—CH₃), 17.9 (Ar—CH₃), 90.3 (C-f), 113.7 (C-b), 117.1, 117.9 (C-d), 122.9, 123.0, 124.2, 127.1 (C-c), 127.9 (C-a), 128.6, 129.8, 130.7, 134.5, 142.3 (C-e), 149.4, 158.9, 161.5 (C-h)*, 162.9 (C-g)*; MS (ESI) 374 (M+1). IR (KBr) ν (cm⁻¹): 3395, 2926, 2582, 1670, 1640, 1550, 1487, 1440, 1402, 1331, 1193, 1078. ESI-HRMS (m/z) [M+H]+ calcd. for $C_{22}H_{20}N_3O_3$ 374.1499, obsd. 374.1501.

N-(2-isopropyl-5-methyl-4-phenoxyphenyl)-2-hydroxypyrazolo[1,5-a]pyridine-3-carboxamide (29). Obtained from 35, flash chromatography (eluent: dichloromethane /methanol/98/2 v/v). White solid (m.p. 244.2-247.9° C. dec.; from trituration with diisopropyl ether). Yield 91%. ¹H NMR (600 MHz, DMSO): δ 1.17 (d, 6H, J=6.8 Hz, —CH(CH₃)₂), 2.10 (s, 3H, —CH₃), 3.10 (hept, 1H, J=6.8 Hz, —CH(CH₃)₂), 6.85 (d, 2H, J=8.0 Hz, aromatic protons), 6.89 (s, 1H, aromatic proton), 6.98 (td, 1H, J=6.9 Hz, 1.1 Hz, H-b), 7.03 (t, 1H, J=7.3 Hz, H-c), 7.33 (t, 1H, J=7.9 Hz, aromatic proton), 7.47 (t, 2H, J=7.8 Hz, aromatic protons), 8.00 (s, 1H, aromatic proton), 8.06 (d, 1H, J=8.8 Hz, H-d), 8.57 (d, J=6.8 Hz, 1H, H-a), 8.98 (s, 1H, —NH), 12.95 (br s, 1H, —OH). ¹³C NMR (151 MHz, DMSO): δ 15.7 (—CH₃), 22.6 (CH(CH₃)₂), 27.3 (—CH(CH₃)₂), 89.4 (C-f), 112.8 (C-b), 115.99, 117.0 (C-d), 117.5, 122.0, 125.7, 127.0, 127.8 (C-c), 129.0 (C-a), 129.9, 131.8, 138.0, 141.5 (C-e), 149.4, 158.0, 161.0 (C-h)*, 162.1 (C-g)*; IR (KBr) ν (cm⁻¹): 3400, 2964, 2579, 1661, 1637, 1547,1492, 1446, 1404, 1332, 1228, 1185, 1130, 887; MS (ESI) 402 (M+1);

General hydrogenation procedure for target compounds 4-6, 30-33. Palladium on carbon (Pd/C, 6% w/w), was added to a solution of the appropriate amide (compounds 22a-c, 1.0 mmol), in dry THF (15 mL), and HCl (1.0 mmol). The resulting mixture was vigorously stirred under a hydrogen atmosphere for 6 hours. The suspension was filtered through Celite and the cake was washed with methanol. The filtrate was concentrated under reduced pressure. When necessary, the obtained solid was further purified by flash chromatography.

2-Hydroxy-N-(2,3,5,6-tetrafluoro-[1,1'-biphenyl]-4-yl)pyrazolo[1,5-a]pyridine-3-carboxamide (4). Obtained from 22a, flash chromatography (eluent: dichloromethane /EtOAc/HCOOH 80:20:1 v/v/v). Pale yellow solid (m.p. 260.9-262.0° C. dec.; from trituration with diisopropyl ether). Yield 87%. ¹H NMR (600 MHz, DMSO): δ 6.93 (t, 1H, J=6.7 Hz, H-b), 7.42 (t, 1H, J=7.7 Hz, H-c), 7.48-7.63 (m, 5H, aromatic protons), 7.90 (d, 1H, J=8.6 Hz, H-d), 8.51 (d, 1H, J=6.6 Hz, H-a), 9.77 (br s, 1H, —NH). Exchangeable proton signals overlapped with the water signal. ¹³C NMR (151 MHz, DMSO): δ 88.9 (C-f), 112.9 (C-b), 116.6 (C-d), 117.1, 117.8, 127.3 (C-c), 127.9, 129.1 (C-a), 129.3, 129.8, 130.7, 142.1, 143.1, 143.8, 161.6 (C-h), 163.9 (C-g); MS (ESI) 402 (M+1). IR (KBr) ν (cm⁻¹): 3383, 3360, 2577, 1676, 1642, 1518, 1492, 1437, 1330, 1269, 1214, 1128, 994. ESI-HRMS (m/z) [M+H]+ calcd. for $C_{20}H_{12}F_4N_3O_2$ 402.0860, obsd. 402.0861.

2-Hydroxy-7-methyl-N-(2,3,5,6-tetrafluoro-[1,1'-biphenyl]-4-yl)pyrazolo[1,5-a]pyridine-3-carboxamide (5). Obtained from 22b, flash chromatography (eluent: dichloromethane /EtOAc/HCOOH 80:20:1). White solid (m.p. 285.9-286.6° C.; from trituration with diisopropyl ether). Yield 86%. ¹H NMR (600 MHz, DMSO): 92.65 (s, 3H, Ar—CH₃), 6.96 (dd, 1H, J=6.9 Hz, 1.7 Hz, H-b), 7.46 (t, 1H J=7.9 Hz, H-c), 7.53-7.66 (m, 5H, aromatic protons), 7.91 (d, 1H, J=8.6 Hz, H-d), 8.94 (s, 1H, —NH); 12.95 (br s, 1H, —OH); ¹³C NMR (151 MHz, DMSO): δ18.0 (Ar—CH₃), 88.8 (C-f), 113.3 (C-b), 115.0 (C-d), 117.6, 119.0, 127.2, 128.8 (C-c), 129.4, 129.9, 130.6, 138.8 (C-a), 142.6 (C-e), 143.5, 145.4, 161.1 (C-h), 163 (C-g); MS (ESI) 416 (M+1). IR (KBr) ν (cm⁻¹): 3379, 3012, 2600, 1697, 1644, 1574, 1548, 1526, 1493, 1439, 1311, 1245, 1167, 1131, 994. ESI-HRMS (m/z) [M+H]+ calcd. for $C_{21}H_{14}F_4N_3O_2$ 416.1017, obsd. 416.1018.

2-Hydroxy-5-methyl-N-(2,3,5,6-tetrafluoro-[1,1'-biphenyl]-4-yl)pyrazolo[1,5-a]pyridine-3-carboxamide (6). Obtained from 22c, flash chromatography (eluent: dichloromethane /EtOAc/HCOOH 80:20:1 v/v/v). White solid (m.p. 287.1-287.5° C. dec.; from trituration with diisopropyl ether). Yield 83%. ¹H NMR (600 MHz, DMSO): δ 2.39 (s, 3H, Ar—CH₃), 6.86 (dd, 1H, J=6.9 Hz, 1.7 Hz, H-b), 7.49-7.60 (m, 5H, aromatic protons), 7.78 (s, 1H, H-d), 8.47 (d, 1H, J=6.9 Hz, H-a), 8.95 (s, 1H, —NH). Exchangeable proton signals overlapped with the water signal. ¹³C NMR (151 MHz, DMSO): 321.0 (Ar—CH₃), 87.4 (C-f), 115.3 (C-b), 115.6 (C-d), 117.0, 126.7, 128.4, 128.8, 129.4 (C-a), 130.1, 139.3 (C-c), 141.7 (C-e), 144.2, 144.8, 160.4 (C-h), 163.0 (C-g); MS (ESI) 416 (M+1). IR (KBr) ν (cm⁻¹): 3381, 3362, 2992, 2590, 1677, 1648, 1517, 1491, 1437, 1334, 1275, 1224, 1123, 993. ESI-HRMS (m/z) [M+H]+ calcd. for $C_{21}H_{14}F_4N_3O_2$ 416.1017, obsd. 416.1019.

2-Hydroxy-N-(2,3,5,6-tetrafluoro-[1,1'-biphenyl]-4-yl)-4,5,6, 7-tetrahydropyrazolo[1,5-a]pyridine-3-carboxamide (30). Palladium on carbon (Pd/C, 20% w/w) was added to a solution of compound 4, 1.0 mmol) in dry THF (10 mL). The resulting mixture was stirred under a hydrogen atmosphere of 40 bar, at temperature of 65° C. for 3 hours using Microwave SynthWAVE. The suspension was filtered through Celite and the cake was washed with methanol. The filtrate was concentrated under reduced pressure. The obtained solid was further purified by flash chromatography (eluent: dichloromethane/EtOAc/HCOOH 80:20:1 v/v/v). White solid (m.p. 270.9-272.9° C. dec.) Yield 40% ¹H NMR (600 MHz, DMSO): δ 1.72-1.78 (m, 2H), 1.91-1.98 (m, 2H), 2.88 (t, 2H, J=6.1 Hz, H-d), 3.82 (t, 2H, J=5.8 Hz, H-a), 7.48-7.54 (m, 5H, aromatic protons), 9.08 (s, 1H, —NH), 11.93 (br s, 1H, —OH). Exchangeable proton signals overlapped with the water signal. $^{13}$C NMR (151 MHz, DMSO): δ 19.03, 22.59, 23.38, 47.04 (C-a), 96.00 (C-f), 117.34, 117.53, 127.17, 129.36, 129.88, 130.62, 142.28, 142.87, 143.84, 145.63, 160.24 (C-g), 161.22 (C-h); MS (ESI) 404.3 (M−1). IR (KBr) ν (cm$^{-1}$): 3338, 2924, 2519, 1685, 1577, 1522, 1437, 1374, 1316, 1283, 1241, 1144, 992.

2-Hydroxy-N-(2,3,3',5,6-pentafluoro-[1,1'-biphenyl]-4-yl)pyrazolo[1,5-a]pyridine-3-carboxamide (32). Obtained from 36b, flash chromatography (eluent: dichloromethane/EtOAc/HCOOH 80:20:1 v/v/v). White solid. Yield 75%. $^1$H NMR (600 MHz, DMSO): δ 7.03 (t, 1H, J=6.6 Hz, H-b), 7.33-7.56 (m, 4H, aromatic protons), 7.62 (dd, 1H, J=14.3, 7.5 Hz, aromatic protons), 7.98 (d, 1H, J=8.6, H-d), 8.62 (d, 1H, J=6.6, H-a), 8.94 (s, 1H, —NH), 12.83 (br s, 1H, —OH); $^{13}$C NMR (151 MHz, CDCl$_3$): δ 88.1 (C-f), 113.3 (C-b), 115.9 (t, J=17.4 Hz), 116.4 (d, J=20.9 Hz), 116.8 (C-d), 117.2 (d, J=23.0 Hz), 117.4 (t, J=14.8 Hz), 126.5, 128.4, 128.7 (d, J=9.6 Hz), 129.2, 130.9 (d, J=8.3 Hz), 141.7, 142.7, 143.2, 160.3 (C-g)*, 162.0 (d, J=244.4 Hz), 162.6 (C-h)*; MS (ESI) 508 (M−1).

2-Hydroxy-N-(2,3,5,6-tetrafluoro-3'-(trifluoromethyl)-[1,1'-biphenyl]-4-yl)pyrazolo[1,5-a]pyridine-3-carboxamide (33). Obtained from 36c, flash chromatography (eluent: dichloromethane/EtOAc/HCOOH 80:20:1 v/v/v). White solid. Yield 98%. $^1$H NMR (600 MHz, CDCl$_3$): δ7.03 (t, 1H, J=6.8 Hz, H-b), 7.51 (t, 1H, J=7.8 Hz, H-c), 7.82 (t, 1H, J=7.8 Hz, aromatic protons), 7.89-8.02 (m, 4H, aromatic protons), 8.62 (d, 1H, J=6.8, H-a), 8.98 (s, 1H, —NH), 12.85 (br s, 1H, —OH); $^{13}$C NMR (151 MHz, CDCl$_3$): δ 88.7 (C-f), 113.8 (C-b), 116.1 (t, J=17.1 Hz), 117.3 (C-d), 118.2 (t, J=12.2 Hz), 124.4 (q, J=271.8 Hz), 126.7 (q, J=3.9 Hz), 127.4, 128.4, 128.9, 129.7, 130.2 (q, J=32.4 Hz), 130.6, 134.9, 142.2, 143.8, 143.9, 160.8 (C-g)*, 163.2 (C-h)*; MS (ESI) 560 (M+1).

Protein expression and purification. The cDNA of the N-truncated form of hDHODH (aa31-395), was amplified from a full length hDHODH I.M.A.G.E. clone (ID 6064723), and inserted into a pFN2A vector (Promega). The vector produces hDHODH as an N-terminal GST-fusion protein. The plasmid pFN2A-hDHODH was transformed into BL21 (DE3), pyrD E. coli cells for protein production. Cells were grown at 37° C. in LB medium supplemented with 0.1 mM flavin mononucleotide. After 20 h of growth, cells were induced with 0.4 mM isopropyl-D-thiogalacto-pyranoside at an OD$_{600}$ of 0.6-0.8 at 28° C. for an additional 3 h. A cell pellet from 300 mL of culture was lysed in 20 ml of PBS (50 mM Na$_2$HPO$_4$, 50 mM NaH$_2$PO$_4$, 500 mM NaCl), which had been supplemented with 24 mg lysozyme and 0.2% v/v protease inhibitor cocktail (Sigma-Aldrich), incubated for 30 min over ice and disrupted by sonication. Triton X-100 was added to the lysate, to a final concentration of 1%, before centrifugation at 14000×g for 40 min at 4° C. The clarified supernatant was incubated with DNase I (Sigma Aldrich), for 30 min at room temperature, supplemented with 2 mM DTT and filtered through a 0.45 μm syringe filter. The GST-fused enzyme was purified from the bacterial lysate using affinity chromatography on immobilized glutathione-sepharose columns and fast protein liquid chromatography (FPLC). The GST tag was not removed for further studies.

hDHODH inhibition assay. Inhibitory activity was assessed by monitoring the reduction of 2,6-dichloroindophenol (DCIP), which is associated with the oxidation of dihydroorotate as catalyzed by the DHODH enzyme. The enzyme was preincubated for five minutes at 37° C. in Tris-buffer solution (pH 8.0), with coenzyme Q10 (100 μM), with the compounds to be tested used at different concentrations (final DMSO concentration 0.1% v/v), with DCIP (50 μM). The reaction was initiated by the addition of DHO (500 μM), and the reduction was monitored at λ=650 nm. The initial rate was measured in the first five minutes (ε=10400 M$^{-1}$ cm$^{-1}$), and an IC$_{50}$ value was calculated,[31] using GraphPad Prism 7 software. Values are means±SE of three independent experiments.

Cell culture and drug treatment. Jurkat cells were cultured in X-VIVO 15 (BE02-060F, Lonza), supplemented with 10% (v/v), fetal bovine serum (F-7524, Sigma Aldrich), and 1% (v/v), antibiotic-antimycotic solution (A-5955, Sigma Aldrich) (complete medium). Cells were maintained at 37° C. in a 5% CO$_2$ humidified atmosphere. Cells were passaged every 2-3 days and discarded after 15 passages. Jurkat cells were routinely tested, to confirm the absence of mycoplasma, using the MycoAlert Plus detection kit (Lonza), and were used for all experiments when in passages 5 and 10. Each compound tested was solubilized in DMSO (drug vehicle, 41639, Fluka), at a final concentration of 10 mM, which was used as the stock solution for all experiments. Final dilutions were made in culture medium.

Proliferation assay. The growth of Jurkat T-cells was evaluated, via the quantitation of DNA content, using the fluorescent dye Hoechst 33258.[32] Cells (5×10$^3$ in 100 μL medium), were seeded in a white 96-well plate and exposed to increasing concentrations (0.001-200 μM), of each compound or vehicle (DMSO), for 72 h. At the end of incubation, the medium was aspirated and the wells washed twice with 100 μL phosphate buffer saline (137 mM NaCl, 2.7 mM KCl, 8.1 mM Na$_2$HPO$_4$, 1.76 mM KH$_2$PO$_4$, PH 7.4). Cells were exposed to 100 μL 0.02% SDS solution in SSC buffer (154 mM NaCl, 15 mM sodium citrate, pH 7), for 1 h at 37° C. with occasional swirling. At the end of the process, an equal volume of 1 μg/mL Hoechst 33258 solution in SSC buffer was added to each well and fluorescence measured at 355 nm (excitation), and 460 nm (emission), using a Fluoroskan Ascent-Thermo microplate fluorometer (Thermo Fisher Scientific, MA). IC$_{50}$ values were determined using nonlinear regression plots on GraphPad Prism6. Values are means±SE of three independent experiments. Where indicated, the antiproliferative effect was evaluated in the presence of 100 μM uridine.[32]

Cytotoxicity assay. The cytotoxic effects that the compounds had on Jurkat T cells were evaluated using the CellTox green assay (Promega). Cells (5×10$^3$/well), were seeded in a white-opaque 96-well plate and exposed to increasing concentrations (0.001-100 μM), of each compound or vehicle (DMSO), for 72 h. Values are means±SE of three independent experiments and represent the concentrations that cause significant (≥30%), cytotoxic effects.

Immunosuppression assay. PBMCs were isolated via the Ficoll/Isopaque (Lymphoprep), density gradient centrifugation of buffy coat leukapheresis residues from the fresh blood samples of healthy donors. Purified cells were grown and maintained in culture medium at 37° C. in a 5% CO$_2$ humidified atmosphere. Cells (5×10$^3$/well), were seeded in a white-opaque 96-well plate and exposed to increasing concentrations (0.001-100 μM), of each compound or vehicle (DMSO), for 2 h and then stimulated with 1.25 mg/ml phytohemagglutinin (PHA) for 72 h. Cell proliferation was assessed via the quantitation of DNA content using the fluorescent dye Hoechst 33258, as described above. IC$_{50}$ values were determined using nonlinear regression plots on GraphPad Prism6. Values are means±SE of three independent experiments. Where indicated, the antiproliferative effect was evaluated in the presence of 100 μM uridine.

Cell lines and drug treatment. Human cells THP1 (acute monocytic leukemia), and U937 (pro-monocytic myeloid leukemia), were cultured in complete RPMI 1640 (Invitrogen Life Technologies, Gaithersburg, MD), supplemented with 10% heat-inactivated fetal bovine serum (FBS), and 1% penicillin/streptomycin (GIBCO, Invitrogen, Milan, Italy).

Flow cytometric analysis. The expression of CD11b (PE-conjugated BD Bioscience San Jose, CA, USA), and CD14 (FITC-conjugated Beckam Coulter CA, USA), cell surface molecules was determined by flow cytometry analysis. Cells were washed and resuspended in staining buffer (phosphate-buffered saline, 2% bovine serum albumin, 1 mM EDTA), and incubated with antibodies at 4° C. for 45 min. Samples were acquired on a FACS Calibur and dead cells were excluded from the analyses, according to the use of propidium iodide (Sigma-Aldrich, Milan, Italy). Data were processed using Kaluza software version 1.2 (Beckman Coulter Fullerton, CA).

CFSE-based cytotoxic activity assay. Briefly, cell lines (THP1 and U937), were incubated with 2 mM carboxyfluorescein diacetate succinimidyl ester dye (CFSE, Vybrant CFDA SE cell tracer kit; Molecular Probes, Invitrogen Carlsbad, CA), at 107/ml for 20 min at 37° C. At the end of the labeling process, cells were resuspended and washed in RPMI-1640 supplemented with 1% fetal bovine serum. Then cells were resuspended in RPMI 1640 supplemented with 10% FBS and incubated for 20 minutes at 37° C. Cells were centrifuged and plated (1×104 in 200 µl of medium), with increasing concentrations of DHODH inhibitors (0.01 µM to 10 µM), for 3 days. The same experiments were repeated in the presence of uridine 100 µM. Cells were harvested and 1 µg/ml of propidium iodide was added to assign the ratio of cell death. The percentage of specific lysis was calculated as described and in accordance with the following equation: [dead targets in sample (%)−spontaneously dead targets (%))/(100−spontaneously dead targets (%))]×100. Spontaneous release was obtained by incubating cell lines in medium supplemented with the corresponding percentage of DMSO used for the dilution of compounds, whereas maximal release was obtained after treatment with triton solution.

Proliferation assay. The proliferation of AML cell lines (THP1 and U937), was evaluated using a flow cytometer. Cell lines were labeled with CFSE dye according to the protocol described above. After labeling, cell lines were plated (1×104), and cultured with DHODH inhibitor molecules (0.01 µM to 10 µM), for three days. At the end of the cultures, cells were harvested and 1p g/ml of propidium iodide was added to exclude dead cells before acquisition. The proliferation of cell lines was quantified on viable cells as % of PI-CSFE-cells.

Differentiation assay. 1×10$^4$ cells (THP1 and U937), were plated in 96 well round-bottom plates and DHODH inhibitors were added, from 0.1 µM to 10 µM, to a volume of 200 µl of medium. The differentiation kinetics was monitored from day 1 to day 4 for U937, and to day 5 for THP1. Cells were washed and either stained with CD11b (U937), or with CD11b and CD14 (THP1), as described above. The differentiation assay was also performed in the presence of uridine 100 µM and analyzed on day 3

Statistical analysis. Statistical analyses were performed on Prism software, version 5.0 (GraphPad Software, San Diego, CA). Data are reported as means±SD. Two tail paired Student's t tests were calculated to assess the differences between mean values and P<0.05 was considered significant.

Solubility assay at pH 7.4. Solubility was assayed both in Phosphate Buffered Saline (PBS: 12 mM with NaCl 137 mM and KCl2.7 mM, pH 7.4), and in PBS with DMSO (2% V/V). Each solid compound (1 mg), was added to 1 mL of PBS or PBS/DMSO. The samples were shaken in an orbital shaker at 25° C. for 24 h. These suspensions were filtered through a PTFE 0.45 m filter (VWR), and the solutions were chromatographically analyzed. Quantitative analysis was performed on a HPLC-UV system (MERK-HITACHI), equipped with an auto sampler of 60 µL injection volume (MERK-HITACHI AS-2000A), a binary HPLC pump (MERK-HITACHI L-6200 IP), and a diode array detector (MERK-HITACHI L-4250). LC analysis was performed using an Agilent Zorbax SB-Phenyl Column (4.6×250, 5 µm). Analyses were carried out at a flow rate of 1 mL/min using gradient elution with eluent A being trifluoroacetic acid (TFA), 0.1% in water and B TFA 0.1% in MeOH for brequinar and compounds 4-10. The analyses started with 40% of eluent B and the following gradient profile was used: (time min, % B) 18.0, 100%; 26.0, 100%; 28.0, 40%. For compound 5, eluent A was TFA 0.1% in water and eluent B acetonitrile. The gradient profile was as follows: (time, % B): 0, 50%; 7.5, 50%; 22.4, 100%; 32.4, 100%. Single compound quantification was made using the relative calibration curve which was obtained by analyzing standard solutions in MeOH. Solubility is expressed as µM concentration of the saturated solution.

C log P and log D (pH 7.4). C log P values were calculated using the Bio-Loom program for Windows, Version 1.5 (BioByte). The partition coefficients between n-octanol and PBS at pH 7.4 (log $D^{7.4}$), were obtained using the shake-flask technique at room temperature. In the shake-flask experiments, 50 mM of phosphate buffered saline pH 7.4 was used as the aqueous phase. The organic (n-octanol), and aqueous phases were mutually saturated by shaking for 4 h. The compounds were solubilized in the buffered aqueous phase at the highest concentration compatible with solubility and appropriate amounts of n-octanol were added. The two phases were shaken for about 20 min, by which time the partitioning equilibrium of solutes had been reached, and then centrifuged (10000 rpm, 10 min). The concentration of the solutes was measured in the aqueous phase by UV spectrophotometer (Varian Cary 50BIO); absorbance values (recorded for each compound at the wavelength of maximum absorption), were interpolated in calibration curves obtained using standard solutions of the compounds ($r^2$>0.99). Each log D value is an average of at least six measurements.

Serum stability. A solution of the selected compound in DMSO was added to human serum (sterile-filtered from human male AB plasma, Sigma-Aldrich), to obtain the desired final concentration with 2% of co-solvent. The resulting solution was shaken in an orbital shaker at 37° C. for 24 h. At appropriate time intervals (0, 0.5, 1, 4 and 24 hours), 300 µL of the reaction mixture were withdrawn and added to 600 µL of trifluoroacetic acid (TFA), 0.1% in acetonitrile in order to deproteinize the serum. The samples were vortexed, sonicated for 3 min and then centrifuged for 5 min at 2500×g. The clear supernatant was filtered and analyzed by RP-HPLC. HPLC analyses were performed on a HP 1100 chromatograph system (Agilent Technologies, Palo Alto, CA, USA), equipped with a quaternary pump (model G1311A), a membrane degasser (G1379A), and a diode-array detector (DAD) (model G1315B), integrated into the HP1100 system. Data analyses were processed using a HP ChemStation system (Agilent Technologies). The analytical column was a ZORBAX Eclipse XDB-C18 (4.6×

150 mm, 5 μm, Agilent Technologies). The mobile phase consisted of acetonitrile 0.10% TFA/0.1% TFA 70/30 at flow-rate=1.0 mL/min. The injection volume was 20 μL (Rheodyne, Cotati, CA). The column effluent was monitored at 245 and 264 nm referenced against a 700 nm wavelength. Single compound quantification was achieved using calibration curves that were obtained by analyzing standard solutions. The results are expressed as % of unmodified parent compound at 24 h.

Protein binding in vitro. Free- and protein-bound drug separation was achieved by ultrafiltration using commercially available membrane systems (Centrifree ultrafiltration devices with ultracel YM-T membrane, Merck). A solution of selected compound in DMSO was added to human serum (sterile-filtered from human male AB plasma, Sigma-Aldrich), to obtain the desired final concentration with 2% of co-solvent. 1 mL of the solution obtained from the sample reservoir of the ultrafiltration device was gently shaken in an orbital shaker at 37° C. for 1 h. The tube was then centrifuged at 1000×g for 25 min. The concentrations of the compounds in the ultrafiltrate and filtrate were determined using reverse-phase HPLC and the chromatographic conditions described above. The quantitation of the compounds in the filtrate was performed using the calibration curves of compound standard solutions (linearity determined in a concentration range of 1-100 μM; $r^2$>0.99). The quantitation of compounds in the ultrafiltrate was performed using calibration curves obtained from the method of standard addition (linearity determined in a concentration range of 0-2.5 μM; $r^2$>0.99). The recovery of the ultrafiltration process was calculated in order to discover whether any compound was lost during ultrafiltration, considering the limited solubility of tested compounds.

$$\text{Recovery} = 100 \times [(\text{vol.}_{bound} \times \text{conc}_{bound}) + (\text{vol.}_{unbound} \times \text{conc}_{unbound})] / \text{vol}_{initial\ serum} \times \text{conc}_{initial}$$

$\text{vol.}_{bound}$: calculated by dividing the weight of the bound fraction (difference between the weights of the sample reservoir after ultrafiltration and empty), by its density (0.991 g/mL assessed by weighing five replicates of a known volume of bound fraction).

$\text{vol.}_{unbound}$: calculated by dividing the weight of the unbound fraction (difference between the weights of the ultrafiltrate cup after and before ultrafiltration), by its density (0.999 g/mL assessed by weighing five replicates of a known volume of unbound fraction).

$\text{conc}_{bound}$: calculated using the RP-HPLC method.

$\text{conc}_{unbound}$: calculated using the RP-HPLC method (calibration with standard additions) Medium recovery was 97% for all tested compounds.

BIBLIOGRAPHY

1. Madak, J. T.; Bankhead, A., 3rd; Cuthbertson, C. R.; Showalter, H. D.; Neamati, N., Revisiting the role of dihydroorotate dehydrogenase as a therapeutic target for cancer. *Pharmacol Ther* 2019, 195, 111-131.
2. Brown, K. K.; Spinelli, J. B.; Asara, J. M.; Toker, A., Adaptive Reprogramming of De Novo Pyrimidine Synthesis Is a Metabolic Vulnerability in Triple-Negative Breast Cancer. *Cancer Discovery* 2017, 7 (4), 391-399.
3. Mathur, D.; Stratikopoulos, E.; Ozturk, S.; Steinbach, N.; Pegno, S.; Schoenfeld, S.; Yong, R.; Murty, V. V.; Asara, J. M.; Cantley, L. C.; Parsons, R., PTEN Regulates Glutamine Flux to Pyrimidine Synthesis and Sensitivity to Dihydroorotate Dehydrogenase Inhibition. *Cancer Discovery* 2017, 7 (4), 380-390.
4. Koundinya, M.; Sudhalter, J.; Courjaud, A.; Lionne, B.; Touyer, G.; Bonnet, L.; Menguy, I.; Schreiber, I.; Perrault, C.; Vougier, S.; Benhamou, B.; Zhang, B.; He, T.; Gao, Q.; Gee, P.; Simard, D.; Castaldi, M. P.; Tomlinson, R.; Reiling, S.; Barrague, M.; Newcombe, R.; Cao, H.; Wang, Y.; Sun, F.; Murtie, J.; Munson, M.; Yang, E.; Harper, D.; Bouaboula, M.; Pollard, J.; Grepin, C.; Garcia-Echeverria, C.; Cheng, H.; Adrian, F.; Winter, C.; Licht, S.; Cornella-Taracido, I.; Arrebola, R.; Morris, A., Dependence on the Pyrimidine Biosynthetic Enzyme DHODH Is a Synthetic Lethal Vulnerability in Mutant KRAS-Driven Cancers. *Cell Chemical Biology* 2018, 25 (6), 705-717.e11.
5. Vyas, V. K.; Variya, B.; Ghate, M. D., Design, Synthesis and Pharmacological Evaluation of Novel Substituted Quinoline-2-Carboxamide Derivatives as Human Dihydroorotate Dehydrogenase (hDHODH) Inhibitors and Anticancer Agents. *Eur J Med Chem* 2014, 82, 385-93.
6. Leban, J.; Vitt, D., Human Dihydroorotate Dehydrogenase Inhibitors, a Novel Approach for the Treatment of Autoimmune and Inflammatory Diseases. *Arzneimittelforschung* 2011, 61 (1), 66-72.
7. Munier-Lehmann, H.; Vidalain, P. O.; Tangy, F.; Janin, Y. L., On Dihydroorotate Dehydrogenases and Their Inhibitors and Uses. *J Med Chem* 2013, 56 (8), 3148-3167.
8. Herrmann, M. L.; Schleyerbach, R.; Kirschbaum, B. J., Leflunomide: an Immunomodulatory Drug for the Treatment of Rheumatoid Arthritis and other Autoimmune Diseases. *Immunopharmacology* 2000, 47 (2-3), 273-289.
9. Singh, A.; Singh, P., Teriflunomide: a Novel Oral Disease-Modifying Agent Under Investigation for the Treatment of Multiple Sclerosis. *J. Drug Deliv. Ther.* 2016, 6 (5), 97-102.
10. Peters, G. J.; Sharma, S. L.; Laurensse, E.; Pinedo, H. M., Inhibition of Pyrimidine De Novo Synthesis by DUP-785 (NSC 368390). *Invest New Drugs* 1987, 5 (3), 235-44.
11. de Forni, M.; Chabot, G. G.; Armand, J. P.; Fontana, X.; Recondo, G.; Domenge, C.; Carde, P.; Barbu, M.; Gouyette, A., Phase I and Pharmacokinetic Study of Brequinar (DUP 785; NSC 368390) in Cancer Patients. *European journal of cancer* (Oxford, England: 1990) 1993, 29A (7), 983-8.
12. Joshi, A. S.; King, S. Y.; Zajac, B. A.; Makowka, L.; Sher, L. S.; Kahan, B. D.; Menkis, A. H.; Stiller, C. R.; Schaefle, B.; Kornhauser, D. M., Phase I Safety and Pharmacokinetic Studies of Brequinar Sodium after Single Ascending Oral Doses in Stable Renal, Hepatic, and Cardiac Allograft Recipients. *J Clin Pharmacol* 1997, 37 (12), 1121-8.
13. Schwartsmann, G.; Dodion, P.; Vermorken, J. B.; ten Bokkel Huinink, W. W.; Joggi, J.; Winograd, B.; Gall, H.; Simonetti, G.; van der Vijgh, W. J.; van Hennik, M. B.; et al., Phase I Study of Brequinar Sodium (NSC 368390) in Patients with Solid Malignancies. *Cancer Chemother Pharmacol* 1990, 25 (5), 345-51.
14. Sykes, D. B.; Kfoury, Y. S.; Mercier, F. E.; Wawer, M. J.; Law, J. M.; Haynes, M. K.; Lewis, T. A.; Schajnovitz, A.; Jain, E.; Lee, D.; Meyer, H.; Pierce, K. A.; Tolliday, N. J.; Waller, A.; Ferrara, S. J.; Eheim, A. L.; Stoeckigt, D.; Maxcy, K. L.; Cobert, J. M.; Bachand, J.; Szekely, B. A.; Mukherjee, S.; Sklar, L. A.; Kotz, J. D.; Clish, C. B.; Sadreyev, R. I.; Clemons, P. A.; Janzer, A.; Schreiber, S. L.; Scadden, D. T., Inhibition of Dihydroorotate Dehydrogenase Overcomes Differentiation Blockade in Acute Myeloid Leukemia. *Cell* 2016, 167 (1), 171-186

15. Lewis, T. A.; Sykes, D. B.; Law, J. M.; Munoz, B.; Rustiguel, J. K.; Nonato, M. C.; Scadden, D. T.; Schreiber, S. L., Development of ML390: A Human DHODH Inhibitor That Induces Differentiation in Acute Myeloid Leukemia. *ACS Med. Chem. Lett.* 2016, 7 (12), 1112-1117.
16. Tzelepis, K.; Koike-Yusa, H.; De Braekeleer, E.; Li, Y.; Metzakopian, E.; Dovey, O. M.; Mupo, A.; Grinkevich, V.; Li, M.; Mazan, M.; Gozdecka, M.; Ohnishi, S.; Cooper, J.; Patel, M.; McKerrell, T.; Chen, B.; Domingues, A. F.; Gallipoli, P.; Teichmann, S.; Ponstingl, H.; McDermott, U.; Saez-Rodriguez, J.; Huntly, B. J. P.; Iorio, F.; Pina, C.; Vassiliou, G. S.; Yusa, K., A CRISPR Dropout Screen Identifies Genetic Vulnerabilities and Therapeutic Targets in Acute Myeloid Leukemia. *Cell Rep* 2016, 17 (4), 1193-1205.
17. Sainas, S.; Pippione, A. C.; Giorgis, M.; Lupino, E.; Goyal, P.; Ramondetti, C.; Buccinna, B.; Piccinini, M.; Braga, R. C.; Andrade, C. H.; Andersson, M.; Moritzer, A. C.; Friemann, R.; Mensa, S.; Al-Kadaraghi, S.; Boschi, D.; Lolli, M. L., Design, synthesis, biological evaluation and X-ray structural studies of potent human dihydroorotate dehydrogenase inhibitors based on hydroxylated azole scaffolds. *Eur J Med Chem* 2017, 129, 287-302.
18. Li, S.; Luan, G.; Ren, X.; Song, W.; Xu, L.; Xu, M.; Zhu, J.; Dong, D.; Diao, Y.; Liu, X.; Zhu, L.; Wang, R.; Zhao, Z.; Xu, Y.; Li, H., Rational Design of Benzylidenehydrazinyl-Substituted Thiazole Derivatives as Potent Inhibitors of Human Dihydroorotate Dehydrogenase with in Vivo Anti-arthritic Activity. *Sci Rep* 2015, 5, 14836-14855.
19. Munier-Lehmann, H.; Lucas-Hourani, M.; Guillou, S.; Helynck, O.; Zanghi, G.; Noel, A.; Tangy, F.; Vidalain, P. O.; Janin, Y. L., Original 2-(3-Alkoxy-1H-pyrazol-1-yl) pyrimidine Derivatives as Inhibitors of Human Dihydroorotate Dehydrogenase (DHODH). *Journal of Medicinal Chemistry* 2015, 58 (2), 860-877.
20. Zhu, J.; Han, L.; Diao, Y.; Ren, X.; Xu, M.; Xu, L.; Li, S.; Li, Q.; Dong, D.; Huang, J.; Liu, X.; Zhao, Z.; Wang, R.; Zhu, L.; Xu, Y.; Qian, X.; Li, H., Design, Synthesis, X-Ray Crystallographic Analysis, and Biological Evaluation of Thiazole Derivatives as Potent and Selective Inhibitors of Human Dihydroorotate Dehydrogenase. *J Med Chem* 2015, 58 (3), 1123-1139.
21. Pippione, A. C.; Dosio, F.; Ducime, A.; Federico, A.; Martina, K.; Sainas, S.; Frolund, B.; Gooyit, M.; Janda, K. D.; Boschi, D.; Lolli, M. L., Substituted 4-Hydroxy-1,2,3-Triazoles: Synthesis, Characterization and First Drug Design Applications Through Bioisosteric Modulation and Scaffold Hopping Approaches. *MedChemComm* 2015, 6 (7), 1285-1292.
22. Lucas-Hourani, M.; Munier-Lehmann, H.; El Mazouni, F.; Malmquist, N. A.; Harpon, J.; Coutant, E. P.; Guillou, S.; Helynck, O.; Noel, A.; Scherf, A.; Phillips, M. A.; Tangy, F.; Vidalain, P. O.; Janin, Y. L., Original 2-(3-Alkoxy-1H-pyrazol-1-yl)azines Inhibitors of Human Dihydroorotate Dehydrogenase (DHODH). *J Med Chem* 2015, 58 (14), 5579-98.
23. Lolli, M. L.; Giorgis, M.; Tosco, P.; Foti, A.; Fruttero, R.; Gasco, A., New inhibitors of dihydroorotate dehydrogenase (DHODH) based on the 4-hydroxy-1,2,5-oxadiazol-3-yl (hydroxyfurazanyl) scaffold. *Eur J Med Chem* 2012, 49, 102-9.
24. Baumgartner, R.; Walloschek, M.; Kralik, M.; Gotschlich, A.; Tasler, S.; Mies, J.; Leban, J., Dual Binding Mode of a Novel Series of DHODH Inhibitors. *J Med Chem* 2006, 49 (4), 1239-1247.
25. Kakehi, A.; Ito, S.; Konno, Y.; Maeda, T., Synthesis Using PyridiniumN-Ylides. I. Synthesis and Some Reactions of Substituted 1-(Acetylimino)pyridinium Ylides. *Bulletin of the Chemical Society of Japan* 1978, 51 (1), 251-256.
26. Ochi, H.; Miyasaka, T.; Kanada, K.; Arakawa, K., Studies of Heterocyclic Compounds. VIII. Synthesis and Tautomerism of 2-Hydroxypyrazolo[1,5-a]pyridine. *Bulletin of the Chemical Society of Japan* 1976, 49 (7), 1980-1984.
27. Minkin, V. I.; Garnovskii, A. D.; Elguero, J.; Katritzky, A. R.; Denisko, O. V., The Tautomerism of Heterocycles: Five-membered Rings with Two or More Heteroatoms. In *Advances in Heterocyclic Chemistry*, Katritzky, A. R., Ed. Academic Press: 2000; Vol. 76, pp 157-323.
28. Pippione, A. C.; Federico, A.; Ducime, A.; Sainas, S.; Boschi, D.; Barge, A.; Lupino, E.; Piccinini, M.; Kubbutat, M.; Contreras, J.-M.; Morice, C.; Al-Karadaghi, S.; Lolli, M. L., 4-Hydroxy-N-[3,5-bis(trifluoromethyl)phenyl]-1,2,5-thiadiazole-3-carboxamide: a Novel Inhibitor of the Canonical NF-κB Cascade. *MedChemComm* 2017, 8 (9), 1850-1855.
29. Sainas, S.; Pippione, A. C.; Giorgis, M.; Lupino, E.; Goyal, P.; Ramondetti, C.; Buccinna, B.; Piccinini, M.; Braga, R. C.; Andrade, C. H.; Andersson, M.; Moritzer, A.-C.; Friemann, R.; Mensa, S.; Al-Kadaraghi, S.; Boschi, D.; Lolli, M. L., Design, synthesis, biological evaluation and X-ray structural studies of potent human dihydroorotate dehydrogenase inhibitors based on hydroxylated azole scaffolds. *Eur. J. Med. Chem.* 2017, 129, 287-302.
30. Williams-Noonan, B. J.; Yuriev, E.; Chalmers, D. K., Free Energy Methods in Drug Design: Prospects of "Alchemical Perturbation" in Medicinal Chemistry. *J Med Chem* 2018, 61 (3), 638-649.
31. Bonomo, S.; Tosco, P.; Giorgis, M.; Lolli, M. L.; Fruttero, R., The role of fluorine in stabilizing the bioactive conformation of dihydroorotate dehydrogenase inhibitors. *J Mol Model* 2013, 19 (3), 1099-107.
32. Cherwinski, H. M.; Cohn, R. G.; Cheung, P.; Webster, D. J.; Xu, Y. Z.; Caulfield, J. P.; Young, J. M.; Nakano, G.; Ransom, J. T., The Immunosuppressant Leflunomide Inhibits Lymphocyte Proliferation by Inhibiting Pyrimidine Biosynthesis. *J Pharmacol Exp Ther* 1995, 275 (2), 1043-9.

What is claimed is:
1. A compound having formula (Ia):

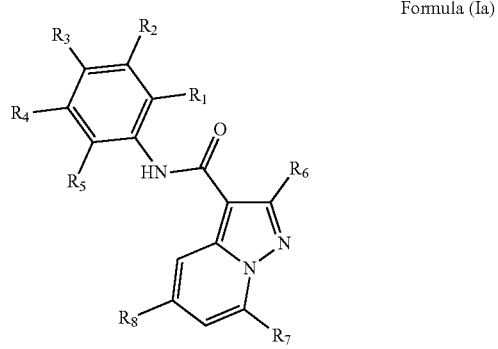

Formula (Ia)

wherein:
$R_1$, $R_2$, $R_4$ and $R_5$ are independently selected from the group consisting of a hydrogen atom, a halogen atom, a $C_1$-$C_4$ alkyl group, and a halo $C_1$-$C_4$ alkyl group;

R$_3$ is selected from the group consisting of phenyl and phenoxy;

R$_7$ and R$_8$ are independently selected from a hydrogen atom and a C$_1$-C$_4$ alkyl group; and R$_6$ is selected from a C$_1$-C$_4$ alkyloxy group, a hydroxyl group, and a salt thereof.

2. The compound of claim 1, wherein X, Y and Z are carbon atoms.

3. The compound of claim 1, wherein at least one of R$_1$, R$_2$, R$_4$ and R$_5$ is or contains a halogen atom.

4. The compound of claim 1, wherein R$_3$ is a phenyl group and each of R$_1$, R$_2$, R$_4$ and R$_5$ is a fluorine atom (F).

5. The compound of claim 1, wherein the C$_1$-C$_4$ alkyl group is a methyl group.

6. The compound of claim 1, wherein the compound is selected from the group consisting of:

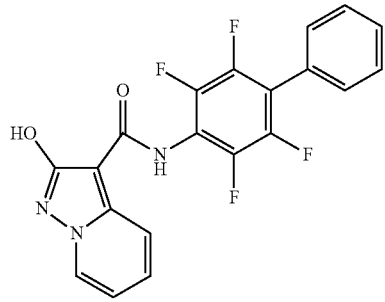

4

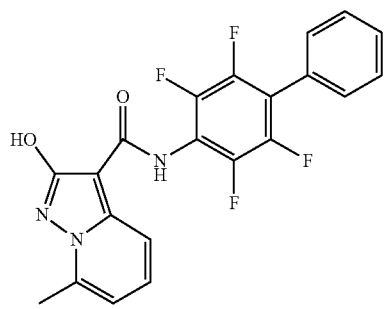

5

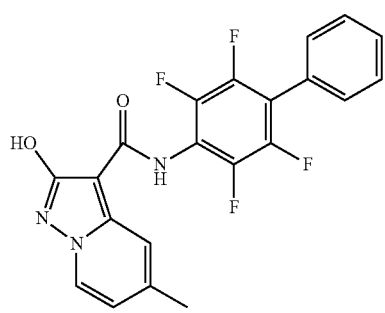

6

-continued

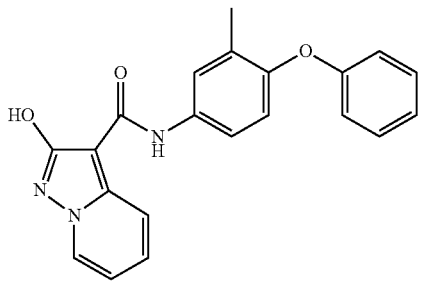

9

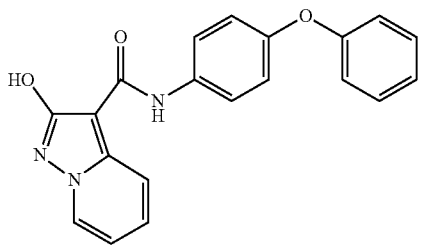

8

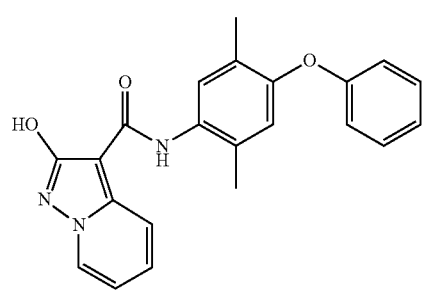

10

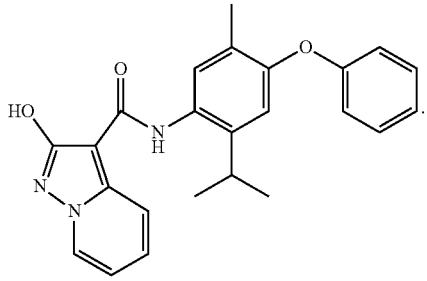

29

7. A method for treating a tumor disease in a subject in need thereof, the method comprising administering to the subject a pharmaceutical composition comprising the compound of claim 6 and a pharmaceutically acceptable carrier, excipient or diluent, wherein the tumor disease is selected from the group consisting of triple-negative breast cancer, PTEN-mutant tumors, and KRAS-driven tumors.

8. A pharmaceutical composition comprising the compound of claim 1 and a pharmaceutically acceptable carrier, excipient or diluent.

9. A method for inhibiting myeloid differentiation in a subject in need thereof, the method comprising administering to the subject a pharmaceutical composition comprising the compound of claim 1 and a pharmaceutically acceptable carrier, excipient or diluent.

10. The method of claim 9, wherein a disease related to inhibiting myeloid differentiation is acute myelogenous leukemia (AML).

11. The compound of claim 1, wherein the compound is:

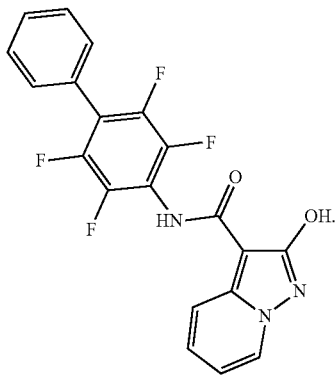

12. A method for treating a tumor disease in a subject in need thereof, the method comprising administering to the subject a pharmaceutical composition comprising the compound of claim 11 and a pharmaceutically acceptable carrier, excipient or diluent, wherein the tumor disease is selected from the group consisting of triple-negative breast cancer, PTEN-mutant tumors, and KRAS-driven tumors.

13. A compound having formula (II):

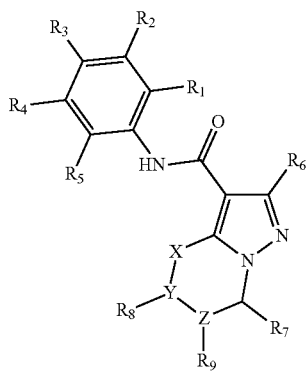

Formula (II)

wherein:
$R_1$, $R_2$, $R_4$ and $R_5$ are independently selected from the group consisting of a hydrogen atom, a halogen atom, a $C_1$-$C_4$ alkyl group, an alkyloxy group, an alkylthio group and a halo $C_1$-$C_4$ alkyl group;
$R_3$ is selected from the group consisting of phenyl, pyridil, pyridinil, phenoxy, pyridiloxy, pyridinoxy, thiophenoxy, thiophenyl, phenylthio, phenylcarboxamido, and a phenylaminocarbonyl group, wherein if $R_3$ is an aromatic group, a substituent independently selected from a halogen atom, an alkyl group, a trifluoromethyl group, and a trifluoromethoxy group can be present on the aromatic group, and wherein if $R_3$ is an aliphatic group, a substituent independently selected from an alkyl group, a trifluoromethyl group, and a trifluoromethoxy group can be present on the aliphatic group;
$R_7$, $R_8$ and $R_9$ are independently selected a halo $C_1$-$C_4$ alkyl group, a thio $C_1$-$C_4$ alkyl group, an amino $C_1$-$C_4$ alkyl group, a $C_1$-$C_4$ alkyl group and a hydroxy $C_1$-$C_4$ alkyl group;
$R_6$ is selected from a $C_1$-$C_4$ alkyloxy group, an aciloxy group, a hydroxyl group, a thiol group and a salt thereof; and X, Y and Z are independently selected from a carbon atom and a nitrogen atom, wherein if X or Y or Z is nitrogen, the other two are carbon atoms.

14. The compound of claim 13, wherein X, Y and Z are carbon atoms.

15. The compound of claim 13, wherein at least one of $R_1$, $R_2$, $R_4$ and $R_5$ is or contains a halogen atom.

16. The compound of claim 13, wherein $R_3$ is a phenyl group and each of $R_1$, $R_2$, $R_4$ and $R_5$ is a fluorine atom (F).

17. The compound of claim 13, wherein the $C_1$-$C_4$ alkyl group is a methyl group.

18. A pharmaceutical composition comprising the compound of claim 13 and a pharmaceutically acceptable carrier, excipient or diluent.

19. A method for treating a tumor disease in a subject in need thereof, the method comprising administering to the subject a pharmaceutical composition comprising the compound of claim 13 a pharmaceutically acceptable carrier, excipient or diluent, wherein the tumor disease is selected from the group consisting of acute myelogenous leukemia (AML), triple-negative breast cancer, PTEN-mutant tumors, and KRAS-driven tumors.

20. A compound having formula (I):

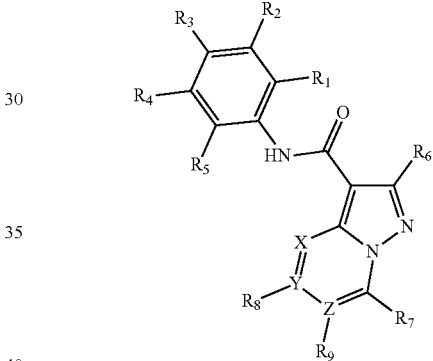

Formula (I)

wherein:
$R_1$, $R_2$, $R_4$ and $R_5$ are independently selected from the group consisting of a hydrogen atom, a halogen atom, a $C_1$-$C_4$ alkyl group, an alkyloxy group, an alkylthio group and a halo $C_1$-$C_4$ alkyl group;
$R_3$ is selected from the group consisting of substituted phenyl, pyridil, pyridinil, pyridiloxy, pyridinoxy, thiophenoxy, thiophenyl, phenylthio, phenylcarboxamido, and a phenylaminocarbonyl group;
$R_7$, $R_8$ and $R_9$ are independently selected from a hydrogen atom, a halo $C_1$-$C_4$ alkyl group, a thio $C_1$-$C_4$ alkyl group, an amino $C_1$-$C_4$ alkyl group, a $C_1$-$C_4$ alkyl group and a hydroxy $C_1$-$C_4$ alkyl group;
$R_6$ is selected from a $C_1$-$C_4$ alkyloxy group, an acyloxy group, a hydroxyl group, a thiol group and a salt thereof;
X is independently selected from a carbon atom and a nitrogen atom; and
Y and Z are carbon atoms.

21. The compound of claim 20, wherein at least one of $R_1$, $R_2$, $R_4$ and $R_5$ is or contains a halogen atom.

22. The compound according to claim 20, wherein $R_3$ is a phenyl group and each of $R_1$, $R_2$, $R_4$ and $R_5$ is a fluorine atom (F).

23. The compound of claim 20, wherein the $C_1$-$C_4$ alkyl group is a methyl group.

24. The compound of claim 20, wherein the compound is selected from the group consisting of:

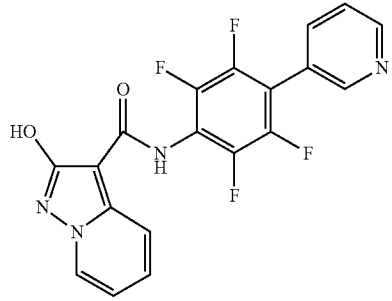

31

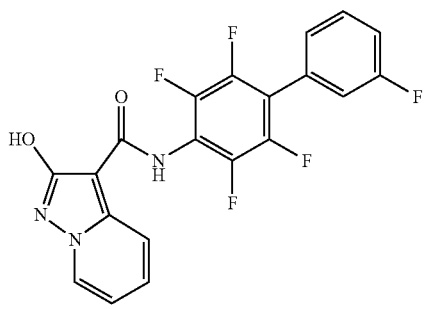

32

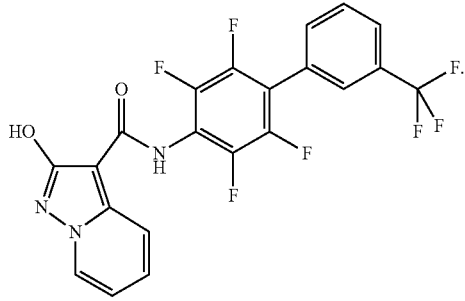

33

25. A pharmaceutical composition comprising the compound of claim 20 and a pharmaceutically acceptable carrier, excipient or diluent.

26. A method for treating a tumor disease in a subject in need thereof, the method comprising administering to the subject a pharmaceutical composition comprising the compound of claim 20 a pharmaceutically acceptable carrier, excipient or diluent, wherein the tumor disease is selected from the group consisting of triple-negative breast cancer, PTEN-mutant tumors, and KRAS-driven tumors.

* * * * *